(12) United States Patent
Franke et al.

(10) Patent No.: US 10,918,864 B2
(45) Date of Patent: Feb. 16, 2021

(54) INTRANASAL STIMULATION FOR TREATMENT OF MEIBOMIAN GLAND DISEASE AND BLEPHARITIS

(71) Applicant: Oculeve, Inc., South San Francisco, CA (US)

(72) Inventors: Manfred Franke, Valencia, CA (US); Diane Michelle Senchyna, Corona del Mar, CA (US); Daniel N. Hamilton, Napa, CA (US)

(73) Assignee: Oculeve, Inc., South San Francisco, CA (US)

(*) Notice: Subject to any disclaimer, the term of this patent is extended or adjusted under 35 U.S.C. 154(b) by 0 days.

(21) Appl. No.: 15/584,956

(22) Filed: May 2, 2017

(65) Prior Publication Data
US 2017/0312521 A1 Nov. 2, 2017

Related U.S. Application Data

(60) Provisional application No. 62/429,059, filed on Dec. 1, 2016, provisional application No. 62/330,763, filed on May 2, 2016.

(51) Int. Cl.
*A61N 1/00* (2006.01)
*A61N 1/36* (2006.01)
*A61N 1/05* (2006.01)

(52) U.S. Cl.
CPC ....... *A61N 1/36046* (2013.01); *A61N 1/0546* (2013.01); *A61N 1/3603* (2017.08); *A61N 1/36014* (2013.01); *A61N 1/36034* (2017.08)

(58) Field of Classification Search
CPC .............. A61N 1/36046; A61N 1/0546; A61N 1/36014
See application file for complete search history.

(56) References Cited

U.S. PATENT DOCUMENTS

| 2,512,882 A | 6/1950 | Truesdale |
| 2,525,381 A | 10/1950 | Tower |
| (Continued) | | |

FOREIGN PATENT DOCUMENTS

| CN | 1488331 A | 4/2004 |
| CN | 2693275 Y | 4/2005 |
| (Continued) | | |

OTHER PUBLICATIONS

Acar, M. et al. (2013). "Ocular surface assessment in patients with obstructive sleep apnea-hypopnea syndrome," Sleep Breath 17(2):583-588.

(Continued)

*Primary Examiner* — Scott M. Getzow
(74) *Attorney, Agent, or Firm* — Mintz Levin Cohn Ferris Glovsky and Popeo, P.C.

(57) ABSTRACT

Described here are devices, systems, and methods for treating meibomian gland disease and/or blepharitis by providing intranasal stimulation. Generally, the devices may deliver electrical stimulation to the nasal mucosa. Intranasal stimulation may unblock obstructed meibomian glands and increase the lipid content of tears, both acutely during stimulation and subsequent to intranasal stimulation. The methods may include an initial round of stimulation to unblock obstructed meibomian glands, and subsequent shorter rounds of stimulation to cause meibum secretion and maintain the open glands.

24 Claims, 24 Drawing Sheets

(56) References Cited

U.S. PATENT DOCUMENTS

| | | |
|---|---|---|
| 3,620,219 A | 11/1971 | Barker |
| 3,709,228 A | 1/1973 | Barker et al. |
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,352,445 A | 10/1994 | Lavaux |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,935,155 A | 8/1999 | Humayun et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,200,626 B1 | 3/2001 | Grobe, III et al. |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,389 B1 | 3/2008 | Newsome |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,032 B1 | 2/2011 | Garito et al. |
| 7,879,079 B2 | 2/2011 | Tu et al. |
| D638,128 S | 5/2011 | Prokop et al. |
| 7,981,095 B2 * | 7/2011 | Grenon ................ A61F 9/0008 604/289 |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |

(56) References Cited

U.S. PATENT DOCUMENTS

| | | | |
|---|---|---|---|
| 8,083,787 B2 * | 12/2011 | Korb | A61F 9/00772 607/1 |
| 8,145,322 B1 | 3/2012 | Yao et al. | |
| 8,155,746 B2 | 4/2012 | Maltan et al. | |
| 8,165,680 B2 | 4/2012 | Greenberg et al. | |
| 8,204,591 B2 | 6/2012 | Ben-David et al. | |
| 8,231,218 B2 | 7/2012 | Hong et al. | |
| 8,251,983 B2 | 8/2012 | Larson et al. | |
| 8,295,529 B2 | 10/2012 | Petersen et al. | |
| 8,318,070 B2 | 11/2012 | Shiah et al. | |
| D681,839 S | 5/2013 | Nathanson | |
| 8,489,189 B2 | 7/2013 | Tronnes | |
| 8,494,641 B2 | 7/2013 | Boling et al. | |
| 8,521,292 B2 | 8/2013 | Wei et al. | |
| 8,626,298 B2 | 1/2014 | Simon | |
| 8,676,324 B2 | 3/2014 | Simon et al. | |
| 8,728,136 B2 | 5/2014 | Feldman | |
| 8,918,181 B2 | 12/2014 | Ackermann et al. | |
| 8,936,594 B2 | 1/2015 | Wolf et al. | |
| 8,986,301 B2 | 3/2015 | Wolf et al. | |
| 8,996,137 B2 | 3/2015 | Ackermann et al. | |
| 9,079,042 B2 | 7/2015 | Tiedtke et al. | |
| 9,095,723 B2 | 8/2015 | Ackermann et al. | |
| 9,265,956 B2 | 2/2016 | Ackermann et al. | |
| 9,440,065 B2 | 9/2016 | Ackermann et al. | |
| 9,687,652 B2 | 6/2017 | Franke et al. | |
| 9,717,627 B2 | 8/2017 | Kuzma et al. | |
| 9,737,702 B2 | 8/2017 | Ackermann et al. | |
| 9,737,712 B2 | 8/2017 | Franke et al. | |
| 9,764,150 B2 | 9/2017 | Loudin et al. | |
| 9,770,583 B2 | 9/2017 | Gupta et al. | |
| 9,821,159 B2 | 11/2017 | Ackermann et al. | |
| 9,956,397 B2 | 5/2018 | Loudin et al. | |
| D826,420 S | 8/2018 | Ackermann et al. | |
| 10,143,846 B2 | 12/2018 | Ackermann et al. | |
| D837,396 S | 1/2019 | Ackermann et al. | |
| 10,207,108 B2 | 2/2019 | Franke et al. | |
| 2001/0018918 A1 | 9/2001 | Burnside et al. | |
| 2001/0020177 A1 | 9/2001 | Gruzdowich et al. | |
| 2002/0013594 A1 | 1/2002 | Dinger et al. | |
| 2002/0035358 A1 | 3/2002 | Wang | |
| 2002/0049290 A1 | 4/2002 | Vanderbilt et al. | |
| 2002/0161416 A1 | 10/2002 | Huang | |
| 2002/0188331 A1 | 12/2002 | Fang et al. | |
| 2003/0014089 A1 | 1/2003 | Chow et al. | |
| 2003/0045909 A1 | 3/2003 | Gross et al. | |
| 2003/0045911 A1 | 3/2003 | Bruchmann et al. | |
| 2003/0114899 A1 | 6/2003 | Woods et al. | |
| 2003/0120323 A1 | 6/2003 | Meadows et al. | |
| 2003/0130809 A1 | 7/2003 | Cohen et al. | |
| 2003/0133877 A1 | 7/2003 | Levin | |
| 2003/0139784 A1 | 7/2003 | Morimoto et al. | |
| 2003/0176892 A1 | 9/2003 | Shalev | |
| 2003/0176898 A1 | 9/2003 | Gross et al. | |
| 2003/0192784 A1 | 10/2003 | Zhou et al. | |
| 2003/0229381 A1 | 12/2003 | Hochmair et al. | |
| 2003/0233134 A1 | 12/2003 | Greenberg et al. | |
| 2003/0233135 A1 * | 12/2003 | Yee | A61N 1/36014 607/48 |
| 2004/0050392 A1 | 3/2004 | Tu et al. | |
| 2004/0059466 A1 | 3/2004 | Block et al. | |
| 2004/0092992 A1 | 5/2004 | Adams et al. | |
| 2004/0098036 A1 | 5/2004 | Bergersen | |
| 2004/0098067 A1 | 5/2004 | Ohta et al. | |
| 2004/0127942 A1 | 7/2004 | Yomtov et al. | |
| 2004/0138646 A1 | 7/2004 | Walla | |
| 2004/0147973 A1 | 7/2004 | Hauser et al. | |
| 2004/0151930 A1 | 8/2004 | Rouns et al. | |
| 2004/0220644 A1 | 11/2004 | Shalev et al. | |
| 2005/0004621 A1 | 1/2005 | Boveja et al. | |
| 2005/0004625 A1 | 1/2005 | Chow | |
| 2005/0010250 A1 | 1/2005 | Schuler et al. | |
| 2005/0010266 A1 | 1/2005 | Bogdanowicz | |
| 2005/0101967 A1 | 5/2005 | Weber et al. | |
| 2005/0101994 A1 | 5/2005 | Yamazaki et al. | |
| 2005/0105046 A1 | 5/2005 | Tung | |
| 2005/0137276 A1 | 6/2005 | Yahiaoui et al. | |
| 2005/0159790 A1 | 7/2005 | Shalev et al. | |
| 2005/0165458 A1 | 7/2005 | Boveja et al. | |
| 2005/0197675 A1 | 9/2005 | David et al. | |
| 2005/0251061 A1 | 11/2005 | Schuler et al. | |
| 2005/0256570 A1 | 11/2005 | Azar | |
| 2005/0267542 A1 | 12/2005 | David et al. | |
| 2005/0268472 A1 | 12/2005 | Bourilkov et al. | |
| 2006/0004423 A1 | 1/2006 | Boveja et al. | |
| 2006/0018872 A1 | 1/2006 | Tew et al. | |
| 2006/0036296 A1 | 2/2006 | Greenberg et al. | |
| 2006/0074450 A1 | 4/2006 | Boveja et al. | |
| 2006/0089673 A1 | 4/2006 | Schultheiss et al. | |
| 2006/0095077 A1 | 5/2006 | Tronnes et al. | |
| 2006/0095108 A1 | 5/2006 | Chowdhury et al. | |
| 2006/0100668 A1 | 5/2006 | Ben-David et al. | |
| 2006/0107958 A1 | 5/2006 | Sleeper | |
| 2006/0142822 A1 | 6/2006 | Tulgar | |
| 2006/0161225 A1 | 7/2006 | Sormann et al. | |
| 2006/0195169 A1 | 8/2006 | Gross et al. | |
| 2006/0206155 A1 | 9/2006 | Ben-David et al. | |
| 2006/0206162 A1 | 9/2006 | Wahlstrand et al. | |
| 2006/0216317 A1 | 9/2006 | Reinhard et al. | |
| 2006/0235430 A1 | 10/2006 | Le et al. | |
| 2006/0239482 A1 | 10/2006 | Hatoum et al. | |
| 2006/0259098 A1 | 11/2006 | Erickson | |
| 2006/0271024 A1 | 11/2006 | Gertner et al. | |
| 2006/0271108 A1 | 11/2006 | Libbus et al. | |
| 2006/0276738 A1 | 12/2006 | Becker | |
| 2007/0031341 A1 | 2/2007 | DiMauro et al. | |
| 2007/0038250 A1 | 2/2007 | He et al. | |
| 2007/0038267 A1 | 2/2007 | Shodo et al. | |
| 2007/0060815 A1 | 3/2007 | Martin et al. | |
| 2007/0060954 A1 | 3/2007 | Cameron et al. | |
| 2007/0083245 A1 | 4/2007 | Lamensdorf et al. | |
| 2007/0112404 A1 | 5/2007 | Mann et al. | |
| 2007/0123938 A1 | 5/2007 | Haller et al. | |
| 2007/0135868 A1 | 6/2007 | Shi et al. | |
| 2007/0150034 A1 | 6/2007 | Rooney et al. | |
| 2007/0219600 A1 | 9/2007 | Gertner et al. | |
| 2007/0237797 A1 | 10/2007 | Peyman | |
| 2007/0237825 A1 | 10/2007 | Levy et al. | |
| 2007/0248930 A1 | 10/2007 | Brawn | |
| 2007/0250119 A1 | 10/2007 | Tyler et al. | |
| 2007/0250135 A1 | 10/2007 | Bartz-Schmidt et al. | |
| 2007/0255333 A1 | 11/2007 | Giftakis et al. | |
| 2007/0276314 A1 | 11/2007 | Becker | |
| 2007/0276451 A1 | 11/2007 | Rigaux | |
| 2007/0295327 A1 | 12/2007 | Bottomley | |
| 2007/0299420 A1 * | 12/2007 | Peyman | A61N 1/30 604/501 |
| 2007/0299462 A1 | 12/2007 | Becker | |
| 2008/0009897 A1 | 1/2008 | Duran Von Arx | |
| 2008/0021515 A1 | 1/2008 | Horsager et al. | |
| 2008/0082057 A1 | 4/2008 | Korb et al. | |
| 2008/0082131 A1 | 4/2008 | Llanos | |
| 2008/0109046 A1 | 5/2008 | Lima et al. | |
| 2008/0109054 A1 | 5/2008 | Hastings et al. | |
| 2008/0114424 A1 | 5/2008 | Grenon et al. | |
| 2008/0132933 A1 | 6/2008 | Gerber | |
| 2008/0132969 A1 | 6/2008 | Bennett et al. | |
| 2008/0140141 A1 | 6/2008 | Ben-David et al. | |
| 2008/0183242 A1 | 7/2008 | Tano et al. | |
| 2008/0183243 A1 | 7/2008 | Shodo et al. | |
| 2008/0208287 A1 | 8/2008 | Palermo et al. | |
| 2008/0208335 A1 | 8/2008 | Blum et al. | |
| 2008/0221642 A1 | 9/2008 | Humayun et al. | |
| 2008/0269648 A1 | 10/2008 | Bock | |
| 2008/0288036 A1 | 11/2008 | Greenberg et al. | |
| 2008/0294066 A1 | 11/2008 | Hetling et al. | |
| 2009/0005835 A1 | 1/2009 | Greenberg et al. | |
| 2009/0012573 A1 | 1/2009 | Karell et al. | |
| 2009/0018582 A1 | 1/2009 | Ishikawa et al. | |
| 2009/0024187 A1 | 1/2009 | Erickson et al. | |
| 2009/0024189 A1 | 1/2009 | Lee et al. | |
| 2009/0036945 A1 | 2/2009 | Chancellor et al. | |
| 2009/0043185 A1 | 2/2009 | McAdams et al. | |
| 2009/0056709 A1 | 3/2009 | Worsoff | |

(56) References Cited

U.S. PATENT DOCUMENTS

| | | |
|---|---|---|
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | DeMaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2009/0312818 A1 | 12/2009 | Horsager et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0100165 A1 | 4/2010 | Swanson et al. |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0256609 A1 | 10/2010 | Hillis et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0311688 A1 | 12/2010 | Chapin et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0076775 A1 | 3/2011 | Stewart et al. |
| 2011/0077551 A1 | 3/2011 | Videbaek |
| 2011/0077698 A1 | 3/2011 | Tsampazis et al. |
| 2011/0081333 A1 | 4/2011 | Shantha et al. |
| 2011/0082518 A1 | 4/2011 | Filippello |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0270067 A1 | 11/2011 | Faraji et al. |
| 2011/0270348 A1 | 11/2011 | Goetz |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2011/0313488 A1 | 12/2011 | Hincapie Ordonez et al. |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0072755 A1 | 3/2013 | Papania et al. |
| 2013/0085551 A1 | 4/2013 | Bachinski et al. |
| 2013/0158451 A1 | 6/2013 | Juto et al. |
| 2013/0158626 A1 | 6/2013 | DeGiorgio et al. |
| 2013/0172790 A1* | 7/2013 | Badawi ............... A61F 7/02 601/15 |
| 2013/0178937 A1 | 7/2013 | Vassallo et al. |
| 2013/0197321 A1 | 8/2013 | Wilson |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1 | 10/2013 | Otto et al. |
| 2013/0282070 A1 | 10/2013 | Cowan et al. |
| 2013/0304154 A1 | 11/2013 | Goodman et al. |
| 2013/0310887 A1 | 11/2013 | Curtis |
| 2013/0336557 A1 | 12/2013 | Cruzat et al. |
| 2014/0012182 A1 | 1/2014 | Shantha et al. |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0148872 A1 | 5/2014 | Goldwasser et al. |
| 2014/0156000 A1 | 6/2014 | Campin et al. |
| 2014/0163580 A1 | 6/2014 | Tischendorf et al. |
| 2014/0214115 A1 | 7/2014 | Greiner et al. |
| 2014/0214118 A1 | 7/2014 | Greiner et al. |
| 2014/0214120 A1 | 7/2014 | Simon et al. |
| 2014/0214124 A1 | 7/2014 | Greiner et al. |
| 2014/0214125 A1 | 7/2014 | Greiner et al. |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0324147 A1 | 10/2014 | Wagner |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0182145 A1 | 7/2015 | Gazdzinski |
| 2015/0238754 A1 | 8/2015 | Loudin et al. |
| 2015/0335900 A1 | 11/2015 | Ackermann et al. |
| 2015/0343202 A1 | 12/2015 | Picaud et al. |
| 2015/0362755 A1 | 12/2015 | Lee et al. |
| 2016/0022992 A1 | 1/2016 | Franke et al. |
| 2016/0058615 A1 | 3/2016 | Camras et al. |
| 2016/0080720 A1 | 3/2016 | Fullam |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |
| 2017/0188947 A1 | 7/2017 | Connor |
| 2017/0239459 A1 | 8/2017 | Loudin et al. |
| 2017/0252563 A1 | 9/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368333 A1 | 12/2017 | Loudin et al. |
| 2017/0368359 A1 | 12/2017 | Loudin et al. |
| 2018/0064940 A1 | 3/2018 | Ackermann et al. |
| 2018/0064941 A1 | 3/2018 | Ackermann et al. |

(56) References Cited

U.S. PATENT DOCUMENTS

| | | |
|---|---|---|
| 2018/0064942 A1 | 3/2018 | Franke et al. |
| 2018/0153394 A1 | 6/2018 | Franke et al. |
| 2018/0154137 A1 | 6/2018 | Ackermann et al. |
| 2018/0154161 A1 | 6/2018 | Ackermann et al. |
| 2018/0161579 A1 | 6/2018 | Franke et al. |
| 2018/0280688 A1 | 10/2018 | Loudin et al. |
| 2019/0022392 A1 | 1/2019 | Franke et al. |
| 2019/0167978 A1 | 6/2019 | Ackermann et al. |
| 2019/0217095 A1 | 7/2019 | Franke et al. |
| 2019/0282804 A1 | 9/2019 | Ackermann et al. |
| 2019/0290922 A1 | 9/2019 | Ackermann et al. |
| 2019/0308009 A1 | 10/2019 | Loudin et al. |
| 2019/0344077 A1 | 11/2019 | Ackermann et al. |
| 2020/0030615 A1 | 1/2020 | Loudin et al. |
| 2020/0038238 A1 | 2/2020 | Kuzma et al. |

FOREIGN PATENT DOCUMENTS

| | | |
|---|---|---|
| CN | 101087822 A | 12/2007 |
| CN | 101503491 A | 8/2009 |
| CN | 101589085 A | 11/2009 |
| CN | 101616663 A | 12/2009 |
| CN | 101829120 A | 9/2010 |
| CN | 101939043 A | 1/2011 |
| CN | 102266592 A | 12/2011 |
| CN | 103467652 A | 12/2013 |
| DE | 102006048819 A1 | 4/2008 |
| EM | 2102681-0001 | 10/2012 |
| EM | 2199000-0001 | 3/2013 |
| EP | 0 109 935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| EP | 3263175 A1 | 1/2018 |
| GB | 2 129 690 B | 3/1987 |
| GB | 2 456 002 A | 7/2009 |
| JP | S60500241 A | 2/1985 |
| JP | S60502192 A | 12/1985 |
| JP | 8-500995 A | 2/1996 |
| JP | 2002-325851 A | 11/2002 |
| JP | 2002-539859 A | 11/2002 |
| JP | 2004-508847 A | 3/2004 |
| JP | 2004526510 A | 9/2004 |
| JP | 2005-502409 A | 1/2005 |
| JP | 2005-052461 A | 3/2005 |
| JP | 2005-144178 A | 6/2005 |
| JP | 2005521489 A | 7/2005 |
| JP | 2005-528169 A | 9/2005 |
| JP | 2006-515900 A | 6/2006 |
| JP | 2006-311917 A | 11/2006 |
| JP | 2007-044323 A | 2/2007 |
| JP | 2007-528751 A | 10/2007 |
| JP | 2008-55000 A | 3/2008 |
| JP | 2008-183248 A | 8/2008 |
| JP | 2008-541850 A | 11/2008 |
| JP | 2009-506836 A | 2/2009 |
| JP | 2009-523503 A | 6/2009 |
| JP | 2010-505563 A | 2/2010 |
| JP | 2010-051562 A | 3/2010 |
| JP | 2010506654 A | 3/2010 |
| JP | 2010-537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| JP | 2012-200558 A | 10/2012 |
| JP | 2013-528416 A | 7/2013 |
| RU | 2338492 C1 | 11/2008 |
| WO | WO-85/01213 A1 | 3/1985 |
| WO | WO-94/00188 A1 | 1/1994 |
| WO | WO-00/01320 A2 | 1/2000 |
| WO | WO-00/56393 A1 | 9/2000 |
| WO | WO-00/62672 A1 | 10/2000 |
| WO | WO-01/05388 A2 | 1/2001 |
| WO | WO-01/85094 A2 | 11/2001 |
| WO | WO-02/078592 A2 | 10/2002 |
| WO | WO-03/023907 A1 | 3/2003 |
| WO | WO-03/082080 A2 | 10/2003 |
| WO | WO-2003/087433 A1 | 10/2003 |
| WO | WO-03/101535 A1 | 12/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/028003 A2 | 3/2007 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/076904 A1 | 7/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2012/174161 A1 | 12/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/162793 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/153218 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |

OTHER PUBLICATIONS

Amparo (2013). "Topical Interleukin 1 Receptor Antagonist for Treatment of Dry Eye Disease," JAMA Ophth. 131(6):E1-E9.
Anonymous (2007). "The epidemiology of dry eye disease: report of the Epidemiology Subcommittee of the International Dry Eye WorkShop (2007)," Ocul. Surf. 5(2):93-107.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.

(56) References Cited

OTHER PUBLICATIONS

Baroody FM, Shenaq D, DeTineo M, et al. Fluticasone furoate nasal spray reduces the nasal-ocular reflex: a mechanism for the efficacy of topical steroids in controlling allergic eye symptoms. J Allergy. Clin Immunol 2009; 123:1342-1348.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth. 45(2):S227-S239.
Cipriano et al. (2014). "Superabsorbent Hydrogels That Are Robust and Highly Stretchable," Am. Chem Soc. 47(13):4445-4452.
Corrected Notice of Allowance dated Feb. 23, 2015, for U.S. Appl. No. 14/256,915, filed Apr. 18, 2014, 2 pages.
Corrected Notice of Allowance dated Jun. 9, 2017, for U.S. Appl. No. 14/920,860, filed Oct. 22, 2015, 2 pages.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nerv Syst 1995;51:109-16.
Elsby et al. (1967). "Lacrimal Secretion in the Cat," Br. J. Pharm. Chemother. 29(1):1-7.
Extended European Search Report dated Nov. 18, 2016, for EP Application No. 14 785 631.4, filed on Apr. 18, 2014, 7 pages.
Final Office Action received for U.S. Appl. No. 14/256,916, dated Apr. 8, 2015, 16 pages.
Final Office Action received for U.S. Appl. No. 14/313,937 dated Apr. 29, 2015, 13 pages.
Final Office Action received for U.S. Appl. No. 14/630,471, dated Sep. 26, 2016, 22 pages.
Final Office Action received for U.S. Appl. No. 14/256,916, dated Aug. 19, 2016, 19 pages.
Final Office Action dated Sep. 23, 2016, for U.S. Appl. No. 14/809,109, filed Jul. 24, 2015, 10 pages.
Final Office Action dated Feb. 1, 2017, for U.S. Appl. No. 14/920,852, filed Oct. 22, 2015, 20 pages.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Heigle TJ, Pflugfelder SC. Aqueous tear production in patients with neurotrophic keratitis. Cornea 1996;15:135-8.
Holzer P. Capsaicin: cellular targets, mechanisms of action, and selectivity for thin sensory neurons. Pharmacol Rev 1991:43:143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dental Mat. J. 27(6):765-774.
International Preliminary Report on Patentability received for PCT Patent Application No. PCT/US2014/034733, dated Oct. 29, 2015.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report dated Feb. 10, 2016, for PCT Patent Application No. PCT/US2015/57021, filed on Oct. 22, 2015, 4 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S Appl. No. 14/313,937, dated Oct. 6, 2015, 7 pages.
Non-Final Office Action Received for U.S Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Notice of Allowance dated May 26, 2017, for U.S. Appl. No. 14/630,471, filed Feb. 24, 2015, 5 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.

(56) References Cited

OTHER PUBLICATIONS

Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016, 5 pages.
Zilstorff-Pedersen (1965). "Quantitative Measurements of the Nasolacrimal Reflex," Arch. Oto. 81:457-462.
Eye Health (2014). "Watery eyes in cold weather," Oregon Eye Specialists, PC, located at http://www.oregoneyes.net/watery-eyes-in-cold-weather/, 3 total pages.
Friedman, N. J. (2010) "Impact of Dry Eye Disease and Impact on Quality of Life." Current Opinion in Ophthalmology. 21:310-316.
Friedman et al. (2016). "A nonrandomized, open-label study to evaluate the effect of nasal stimulation on tear production in subjects with dry eye disease," Clin. Ophthal. 10:795-804.
Galor, A. et al. (2014). "Environmental factors affect the risk of dry eye syndrome in a United States veteran population," Opth. 121:972-973.
Harvard Health Publishing (2010). "Dry eyes and what you can try," Harvard Medical School, 2 total pages.
McDonald, MD, Marguerite et al. "Hydroxpropyl Cellulose Ophthalmic Inserts (Lacrisert) Reduce the Signs and Symptoms of Dry Eye Syndrome and Improve Patient Quality of Life." *Transactions of the American Ophthalmological Society*, (2009), 107:214-222.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
van Setten, G. et al. (2016). "Evidence of seasonality and effects of psychrometry in dry eye disease," Acta Opth. 94:499-506.
Vapor Pressure Data for H2O (2012). Handbook of Chemistry and Physics, 73rd edition, 1 total page.
Yu, PhD, Junhua, et al. "The Economic Burden of Dry Eye Disease in the United States: a Decision Tree Analysis." *Cornea*, (Apr. 2011), 30(4):379-387.
Ahmed, E. M. et al. (2013, e-published Jul. 18, 2013). "Hydrogel: Preparation, characterization, and applcations: A review," Cairo University, Journal of Advanced Research (2015) 6, 105-121.
Olsen et al. (1998) "Human Sclera: Thickness and Surface Area." American Journal of Ophthalmology. Feb. 1998, vol. 125, Issue 2, pp. 237-241.

* cited by examiner

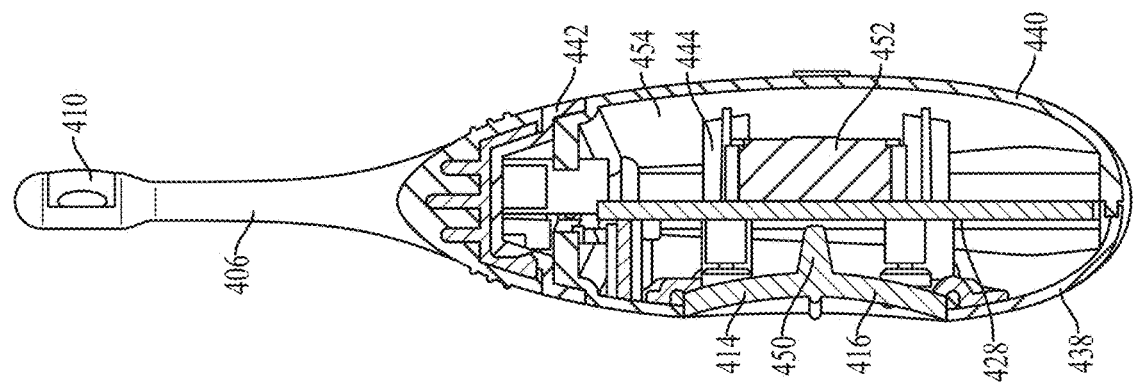
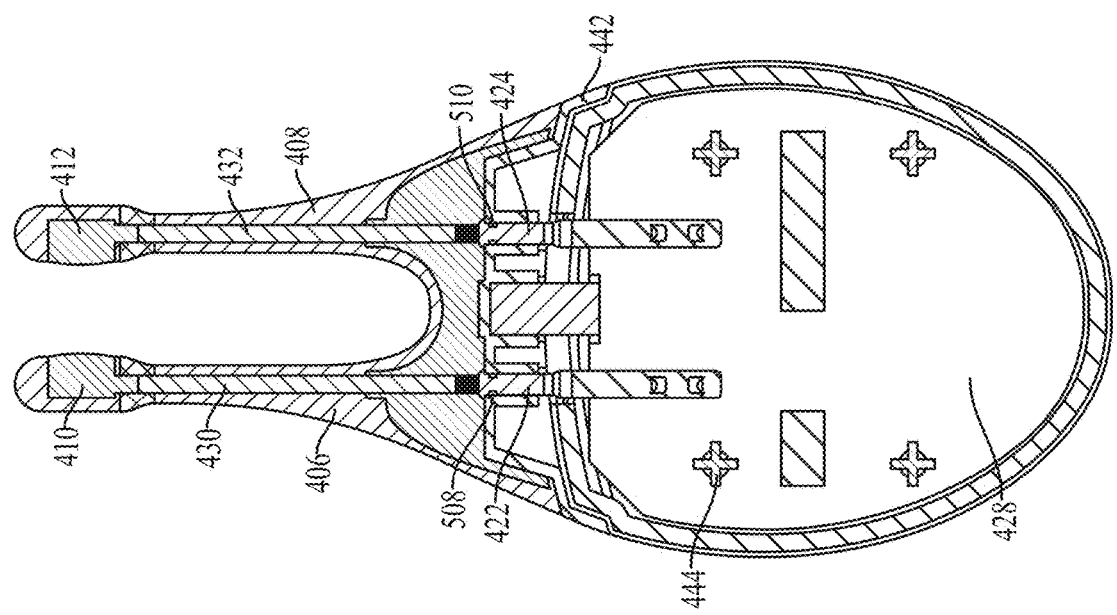

INTRANASAL STIMULATION FOR TREATMENT OF MEIBOMIAN GLAND DISEASE AND BLEPHARITIS

CROSS-REFERENCE TO RELATED APPLICATIONS

This application claims priority to U.S. Provisional Application No. 62/330,763, filed May 2, 2016, and titled "INTRANASAL STIMULATION FOR TREATMENT OF MEIBOMIAN GLAND DYSFUNCTION AND BLEPHARITIS," and to U.S. Provisional Application No. 62/429,059, filed Dec. 1, 2016, and titled "INTRANASAL STIMULATION FOR TREATMENT OF MEIBOMIAN GLAND DYSFUNCTION AND BLEPHARITIS," each of which is hereby incorporated by reference in its entirety.

FIELD

Described here are devices, systems, and methods for treating meibomian gland disease/dysfunction and/or blepharitis using intranasal stimulation.

BACKGROUND

The meibomian glands are large sebaceous glands located in the tarsal plates of the upper and lower eyelids. Typically, the glands generate lipids (meibum), which are excreted onto the eyelid margin through excretory ducts during muscular contractions from eyelid movement. In patients with meibomian gland disease/dysfunction, abnormalities of the meibomian glands may result in reduced or no glandular secretions, and/or the meibum that is secreted may have an altered chemical composition. As a result of these changes, a reduction in quantity and/or quality of meibum in the tear film layer may result in instability of the tear film, increased tear evaporation, hyperosmolarity of the tears, and/or alteration of the ocular surface. Patients with meibomian gland disease/dysfunction may experience symptoms such as eye irritation, ocular discomfort, itching, and/or photophobia, and the like, as well as signs described as inflammation, reduced tear film volume, and ocular surface disease. The risk of meibomian gland disease/dysfunction may increase with certain risk factors, including age, reduced local androgen concentration, certain racial backgrounds, use of certain medications, wearing of contact lenses, and/or wearing of eye makeup.

Currently, common treatment approaches for meibomian gland disease/dysfunction include eyelid hygiene, warm compresses, massaging of the eyelid, lubricants, topical or oral antibiotics, meibomian gland probing, meibomian gland expression gland probing, and simultaneous application of heat and pulsatile pressure to the eyelids. Despite the prevalence of meibomian gland disease/dysfunction, however, these treatment approaches have had limited success. It would therefore be desirable to have an improved treatment for meibomian gland disease/dysfunction.

BRIEF SUMMARY

Described here are devices, systems, and methods for treating meibomian gland disease/dysfunction and/or blepharitis using intranasal stimulation. In general, the methods described herein may increase meibum secretion in a subject. The methods may comprise delivering intranasal electrical stimulation to a subject having meibomian gland disease and/or blepharitis for at least three minutes. The stimulation may cause the number of meibomian glands of the subject that are secreting meibum to increase during intranasal electrical stimulation, as compared to the number of meibomian glands secreting meibum before the intranasal electrical stimulation. In some variations, the intranasal electrical stimulation may be delivered for at least five minutes. In some variations, the intranasal electrical stimulation may be delivered for at least eight minutes. The stimulus may comprise a waveform having one or more off periods. The off periods may be between about 1 second and about 30 seconds, and may result in a pumping action of the orbicularis muscles to expel meibum. The methods may also comprise delivering intranasal electrical stimulation a second time. The duration of the second stimulation delivery may be shorter than the duration of the first stimulation delivery. In some instances the second duration may be at least three minutes. Repeated delivery of intranasal electrical stimulation for sufficient durations (e.g., at least about three minutes) may result in strengthening of the orbicularis muscle. In some variations, the duration of stimulus delivery may be verified by measuring impedance or an electromyogram (EMG) signal. The EMG signal may be measured from a facial muscle. The facial muscle may be near the nose, cheeks, or around the eyes of the subject.

In the methods described herein, the intranasal electrical stimulation may be delivered using a stimulator comprising at least one nasal insertion prong. In some variations the stimulator may comprise two nasal insertion prongs. A portion of a nasal insertion prong may be placed in contact with the nasal mucosa. In some variations, the portion of the nasal insertion prong placed in contact with the nasal mucosa may comprise a hydrogel electrode. The stimulator may in some variations have features to assist with hands-free or reduced-handling use. For example, the stimulator may comprise a strap to hold the nasal insertion prong in the nose. In some variations in which the stimulator comprises two nasal insertion prongs, the nasal insertion prongs may be biased toward each other. This bias may hold the stimulator in the nose during delivery of the intranasal electrical stimulation. In some variations, the intranasal electrical stimulation may be delivered using a stimulator that is temporarily attached to the nasal septum of the subject during delivery. In yet other variations, the intranasal electrical stimulation may be delivered by an implanted microstimulator. The implanted microstimulator may be implanted within a layer of submucosa.

One of a plurality of electrical stimuli may be selected for intranasal delivery. In some variations the selection may be based on perceived paresthesia, and/or it may be based on meibum expression during delivery (e.g., by visualization of the lower eyelid margin during intranasal electrical stimulation).

Intranasal electrical stimulation may be used in conjunction with other treatments for meibomian gland disease and/or blepharitis. In some variations, the methods may comprise administering an additional treatment for meibomian gland disease. The additional treatment may comprise application of a warm compress, eyelid massage, and/or use of eyelid wipes. In some variations, the method may comprise administering additional treatment for blepharitis.

Methods described herein may also treat a subject having meibomian gland disease and/or blepharitis by visualizing an eyelid margin of the subject during intranasal electrical stimulation of the subject. The stimulation may be stopped, or the subject may be instructed to stop stimulation, after the observation of meibum secretion onto the eyelid margin.

The visualization may be performed with any suitable modality, such as a slit lamp or video capture. One or more parameters of the electrical stimulation may be adjusted during visualization. The stimulation may be delivered by a stimulator. In some variations the stimulator may comprise a user interface configured to adjust at least one parameter of the electrical stimulation. Additionally or alternatively, the stimulator may comprise a remote interface configured to adjust at least one parameter of the electrical stimulation. The remote interface may be used to adjust at least one parameter of the electrical stimulation while visualizing the eyelid margin.

Methods described herein may also treat a subject having meibomian gland disease and/or blepharitis by visualizing an eyelid margin of the subject during intranasal electrical stimulation of the subject, and adjusting at least one parameter of the intranasal electrical stimulation based on the visualization. The visualization may be performed with any suitable modality, such as a slit lamp or video capture. The intranasal electrical stimulation may increase secretion of meibum from the meibomian glands, such that the number of meibomian glands of the subject secreting meibum during the intranasal electrical stimulation is greater than the number of meibomian glands of the subject secreting meibum before the intranasal electrical stimulation. Adjusting at least one parameter of the intranasal electrical stimulation may comprise changing a first stimulation waveform to a second stimulation waveform. Changing from the first waveform to the second waveform may result in more uniform meibum expression between the two eyes of the subject. That is, the difference between the number of meibomian glands of the first eye of the subject secreting meibum and the number of meibomian glands of the second eye of the subject secreting meibum during intranasal electrical stimulation with the first stimulation waveform may be larger than the difference between the number of meibomian glands of the first eye secreting meibum and the number of meibomian glands of the second eye secreting meibum during intranasal electrical stimulation with the second stimulation waveform.

The methods described herein may also include treating dry eye by intranasally delivering electrical stimulation to a subject afflicted with dry eye, obtaining feedback relating to the efficacy of the delivered electrical stimulation by measuring impedance or an electromyogram (EMG) signal from a facial muscle near the nose, cheeks, or around the eyes of the subject, formulating a treatment plan based on the feedback, and continuing intranasal delivery of the electrical stimulation according to the treatment plan, wherein the delivered electrical stimulation increases the release of meibum to treat the dry eye of the subject. The impedance or the EMG signal may be measured intranasally by a device that delivers the electrical stimulation, or the impedance or the EMG signal may be measured using an extranasal device. In some variations the extranasal device may comprise a nose strip. The nose strip may comprise detection electrodes. In some variations, formulating the treatment plan may further comprise optimizing one or more parameters of the electrical stimulation. The one or more parameters may be selected from the group consisting of duration of stimulation, type of stimulation waveform, frequency of the stimulation waveform, amplitude of the stimulation waveform, pulse width of the stimulation waveform, and combinations thereof.

The methods described herein may also include treating dry eye by determining that a subject afflicted with dry eye is deficient in meibum secretion, and intranasally delivering an electrical stimulation to the subject, where the intranasally delivered electrical stimulation is effective to increase the secretion of meibum. In some variations, the duration of stimulation may be between about three minutes and about five minutes. The duration of stimulation may in some instances be verified by measuring impedance or an electromyogram signal from a facial muscle near the nose, cheeks, or around the eyes of the subject.

The methods described herein may also include treating dry eye by repeatedly delivering intranasal electrical stimulation to a subject over a period of time, wherein the subject has meibomian gland disease, and wherein the intranasal electrical stimulation is effective to improve secreted meibum quality. In some variations, the period of time is at least 30 days. In other variations, the period of time is at least 45 days, at least 60 days, or at least 90 days. The intranasal stimulation may be delivered consistently and repeatedly over the period of time, such as at least once daily over the period of time. In some variations, the improvement in secreted meibum quality comprises an increased number of lower lid meibomian glands secreting clear meibum at the end of the period of time (e.g., at 30 days) as compared to the beginning of the period of time (e.g., at 0 days).

BRIEF DESCRIPTION OF THE DRAWINGS

FIGS. 4A, 4B, 4C, 4D, and 4E show perspective, front, back, cut-away back, and cut-away side views, respectively, of an illustrative variation of a stimulator.

FIG. 9A shows a front view of the stimulator body docked in the base station, while FIGS. 9B, 9C, and 9D depict side, back, and top views, respectively, of the base station.

DETAILED DESCRIPTION

Figure 1:
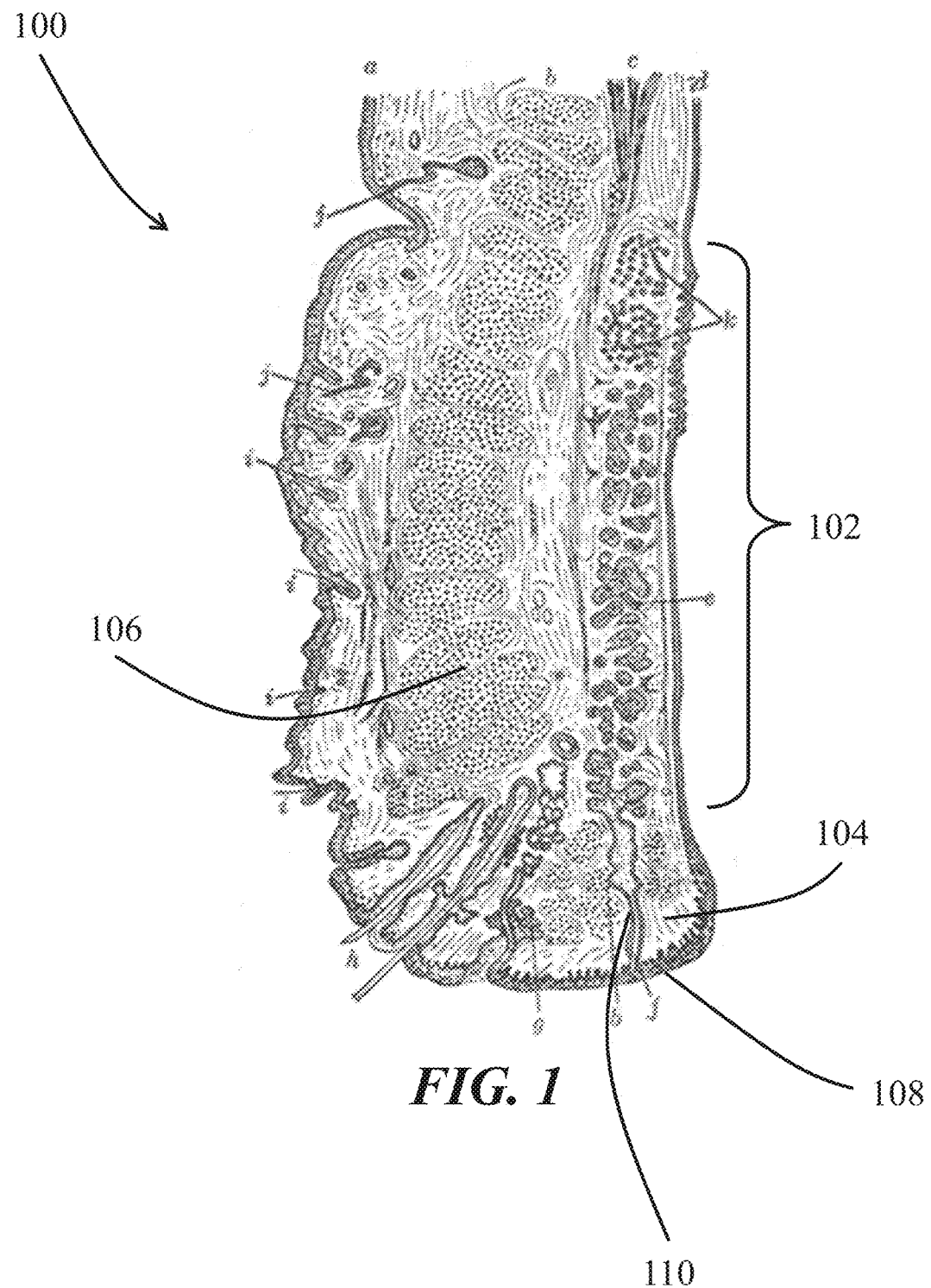
FIG. 1 shows a sagittal cross-section through an upper eyelid.

Described here are devices, systems, and methods for treating meibomian gland disease/dysfunction and/or blepharitis using intranasal stimulation. More particularly, the devices, systems, and methods may be configured to deliver an electrical stimulus to the nasal mucosa to cause meibum secretion or otherwise treat meibomian gland disease/dysfunction. The meibomian glands are large sebaceous glands located in the tarsal plates of the upper and lower eyelids. FIG. 1 is a sagittal cross-section through an upper eyelid 100, showing a meibomian gland 102, the Riolan's muscle 104, and the orbicularis muscle 106. Typically, the meibomian glands 102 generate lipids (meibum), which are excreted onto the lid margin 108 through excretory ducts 110. As the orbicularis muscle 106 contracts, it squeezes the meibomian gland 102. If the Riolan's muscle 104, a sphincter muscle at the opening of the meibomian gland, is relaxed during contraction of the orbicularis muscle 106, meibum may be expressed from the gland.

In patients with meibomian gland disease/dysfunction/posterior blepharitis, however, abnormalities of the meibomian glands may result in reduced or no glandular secretions, and/or the meibum that is secreted may have an altered chemical composition. As a result of these changes, there may be a reduction in quantity and/or quality of meibum in the tear film layer. In some variations, the methods described herein may use application of intranasal stimulation to unblock the openings of the meibomian glands, and/or to keep the openings from becoming obstructed. Additionally or alternatively, the methods described herein may use intranasal stimulation to expel meibum from the meibomian glands and onto the eyelid margin. Additionally or alternatively, the methods described herein may use intranasal stimulation to generate sustained increases in quantity of meibum secretion (i.e., increased meibum secretion not during stimulation), and thus sustained changes in tear composition such that the tears have higher lipid content. Additionally or alternatively, the methods described herein may use intranasal stimulation to improve the quality of meibum secretions.

Intranasal stimulation may in part treat meibomian gland disease/dysfunction through generating coordinated muscle contraction and relaxation. More particularly, afferent neurostimulation with particular waveforms (described in detail elsewhere herein) may cause the orbicularis muscle to contract to generate pressure around the meibomian glands. This pressure, when the Riolan's muscle remains relaxed, may result in meibum expression and/or may help to unblock obstructed portions of the glands.

It should be appreciated that direct electrical muscle activation of muscles in the eyelids, in contrast to afferent neurostimulation, may result in contraction of both the orbicularis muscle and Riolan's muscle. As such, unlike afferent neurostimulation achievable with intranasal stimulation, direct muscle activation may not have the desired effect of contraction of the orbicularis muscle without contraction of the Riolan's muscle. Moreover, afferent neurostimulation with intranasal stimulation may result in activation of both large and small muscle fibers in the orbicularis muscle, resulting in less fatigue than direct muscle activation, since direct muscle activation may activate only large muscle fibers. Repeated and/or sustained intranasal stimulation over a period of time may also strengthen the orbicularis muscle, resulting in increased pressure generated around the meibomian gland upon contraction. This may result in an increased ability to eject meibum plugs that may be occluding the opening of the gland, and/or may result in greater ejection of meibum upon contraction. This effect may be seen both during acute intranasal stimulation and when no stimulation is applied. Furthermore, repeated intranasal stimulation over a period of time may also result in improved quality of secreted meibum.

Figure 2A:
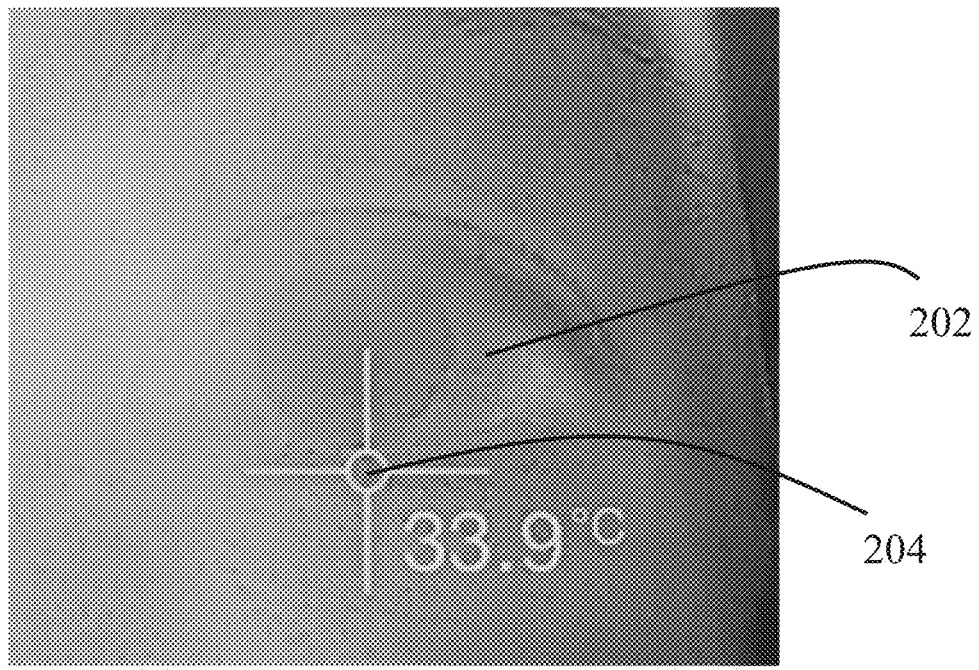
FIGS. 2A-2B show temperature maps of the eye and surrounding area of the face of a subject before and during intranasal stimulation, respectively.
Figure 2B:
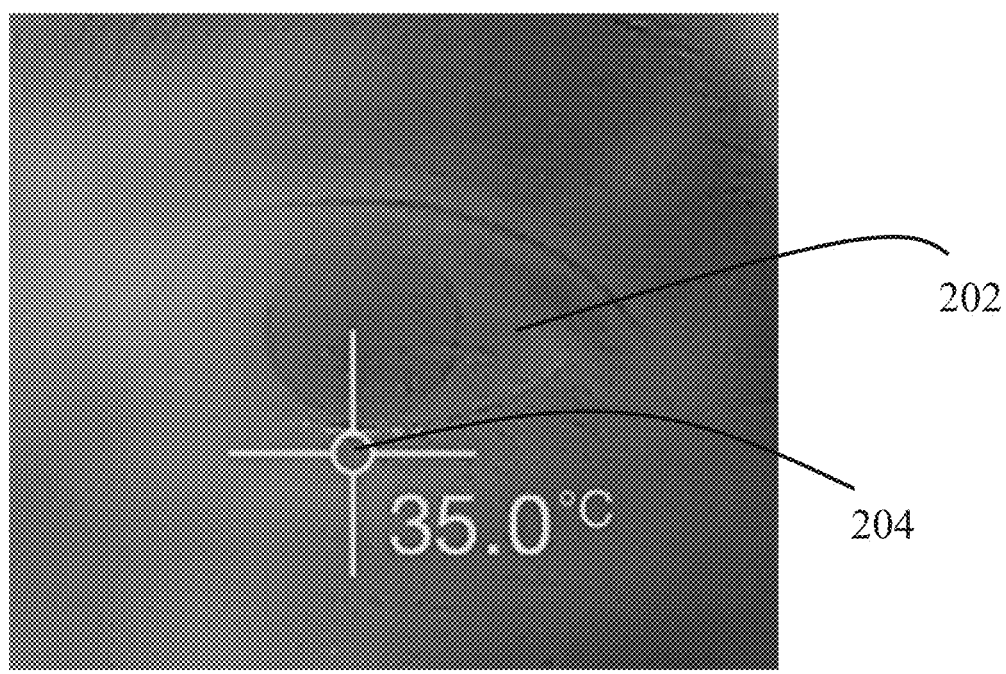
Figure 3:
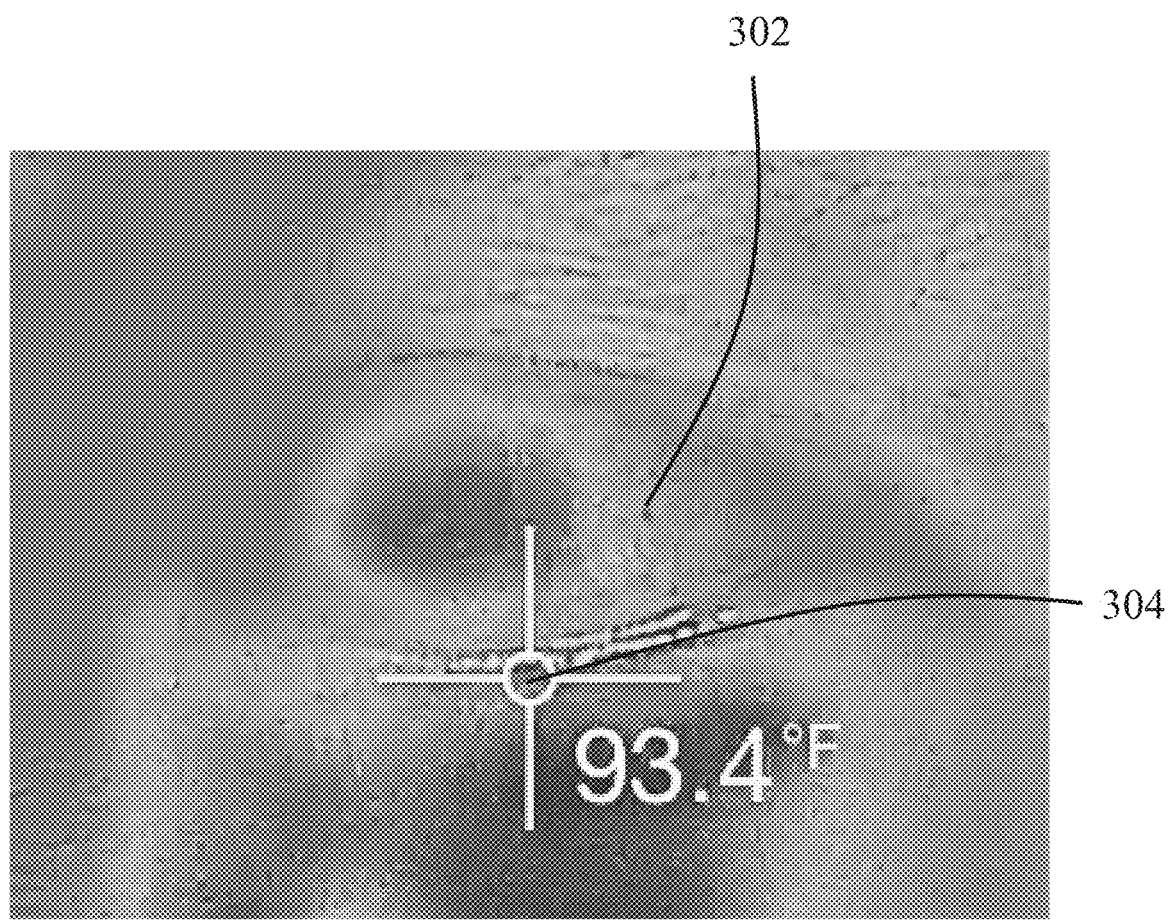
FIG. 3 shows a temperature map of the eye and surrounding area of the face of a different subject during intranasal stimulation.
Figure 4A:
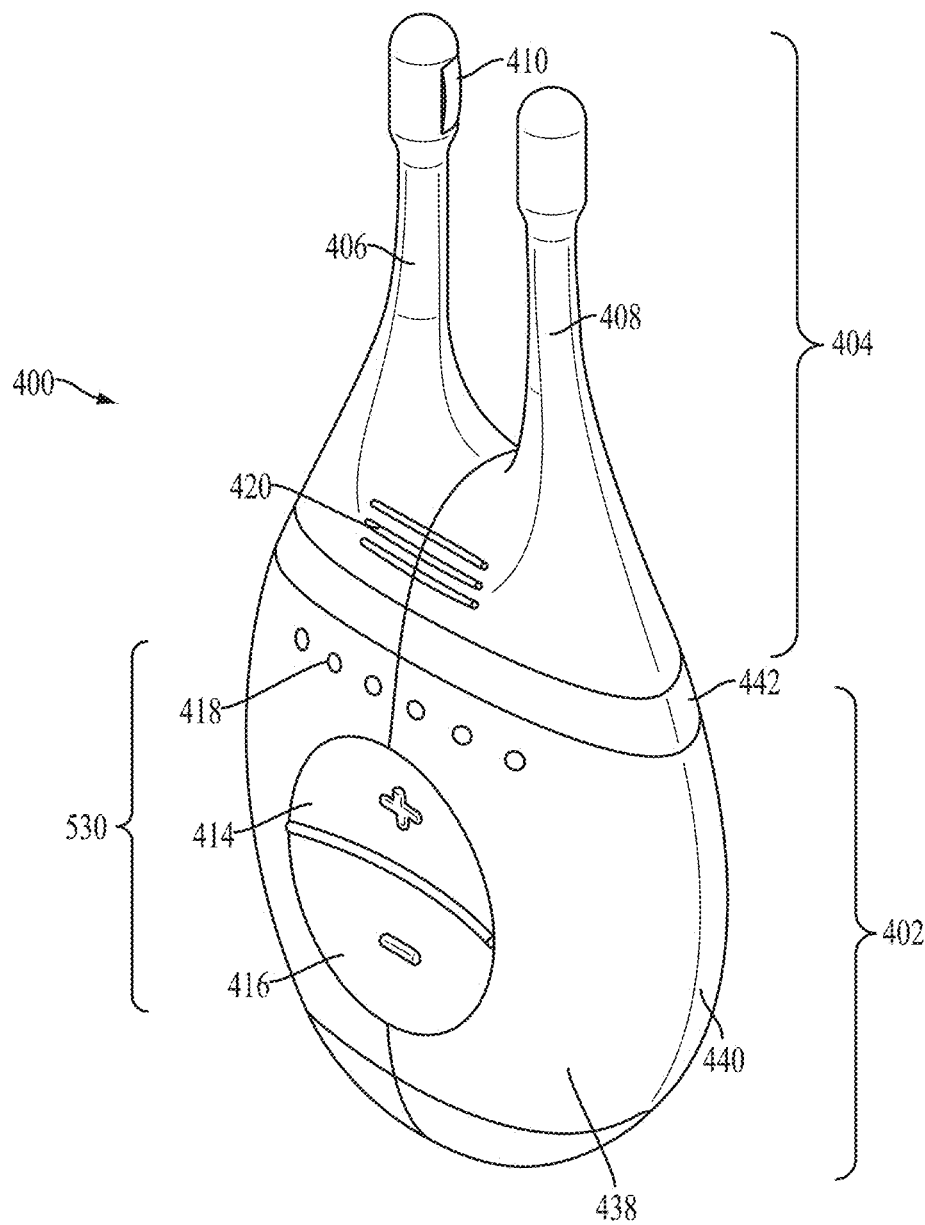
Figure 4C:
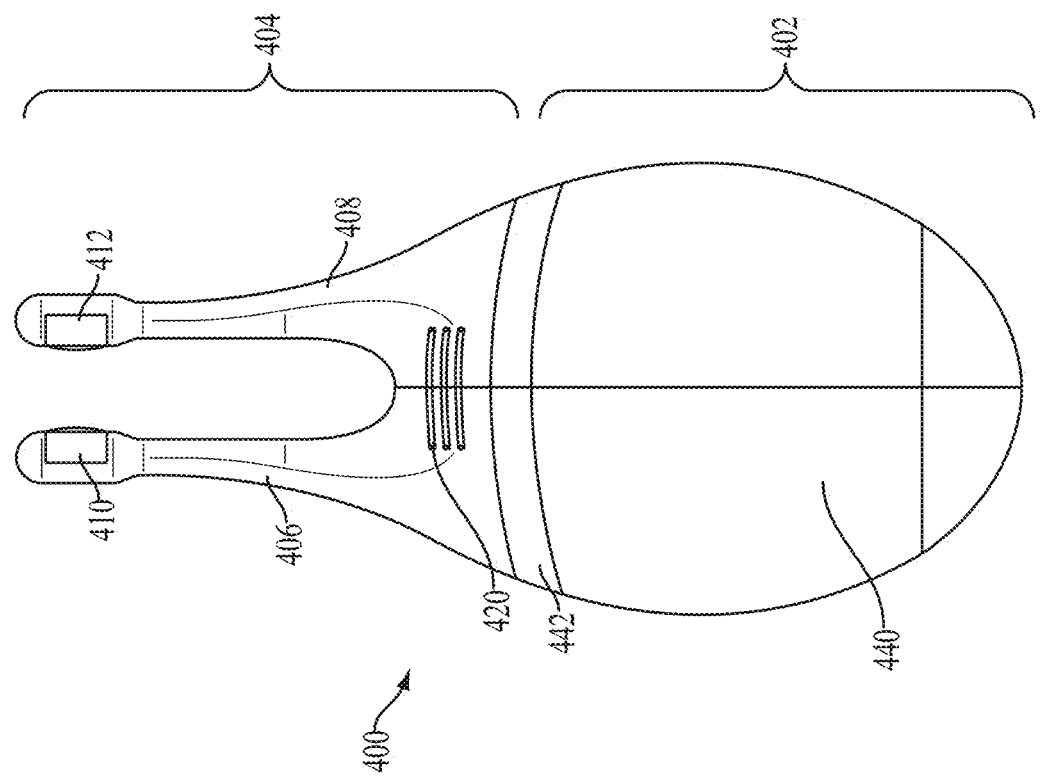
Figure 4B:
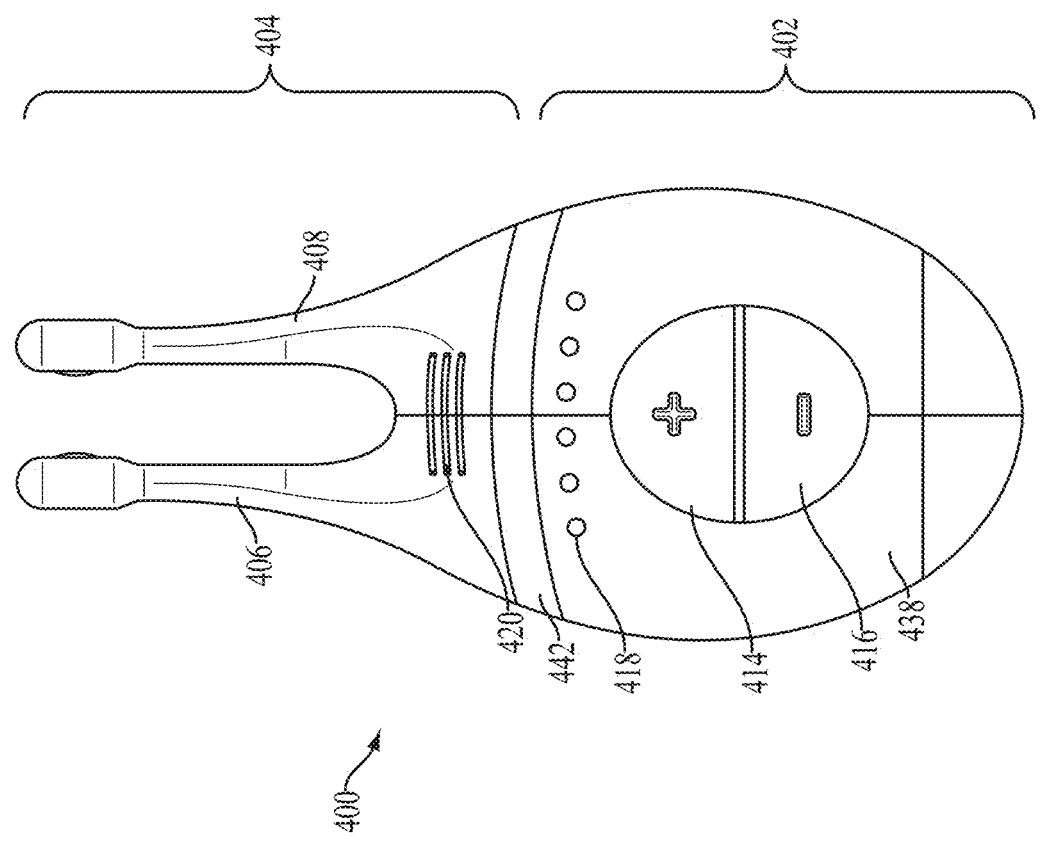

Intranasal stimulation may also in part treat meibomian gland disease/dysfunction through selectively heating the meibomian glands and surrounding tissue (e.g., the eyelids). FIGS. 2A-2B show temperature maps of the eye 202 and surrounding area of a subject before and during intranasal stimulation, respectively. As shown there, before intranasal stimulation, the temperature of the lower eyelid 204 is about 33.9° C. After about 30 seconds of intranasal stimulation, the temperature of the lower eyelid 204 is about 35.0° C. Similarly, FIG. 3 shows a temperature map of an eye 302 and surrounding area of the face of a different subject during intranasal stimulation. There, the temperature of the lower eyelid 304 is about 34.1° C. after about 2 minutes of intranasal stimulation. This heating may be due to muscle activity of the orbicularis muscle. However, unlike application of an external heat source, heating of the eyelid from muscle activity may specifically heat the area where meibum is located, without exposing the cornea, conjunctiva, eye, or skin of the eyelid to excessive heat.

Heating of the meibomian glands may cause meibum inside the glands to warm, thereby lowering its viscosity and causing it to expand. These effects may contribute, along with contraction of the orbicularis muscle, to loosening and expelling of meibum plugs from the glands and unblocking of the opening of the gland, as well as to increased ejection of meibum upon contraction of the orbicularis muscle. Loosening and expelling of meibum from within the glands may also in some instances remove bacteria from the glands and thus provide treatment for posterior blepharitis. These effects may be achieved without risk of corneal abrasion (e.g., without a device in contact with any portion of the cornea or conjunctiva) and without the discomfort associated with physical manipulation of the eyelids.

In addition to causing acute secretion of meibum during intranasal stimulation, delivery of intranasal stimulation over one or more treatment periods may have a sustained effect on meibum secretion onto the eyelid margin. That is, even after cessation of intranasal stimulation, a subject having had intranasal stimulation delivered may experience an increase in quantity and/or quality of meibum secretion, and in turn, increased lipid content in the tear film. This effect may be observed for an extended period of time after a single intranasal stimulation session or after a treatment regimen.

Devices and Systems

Figure 5:
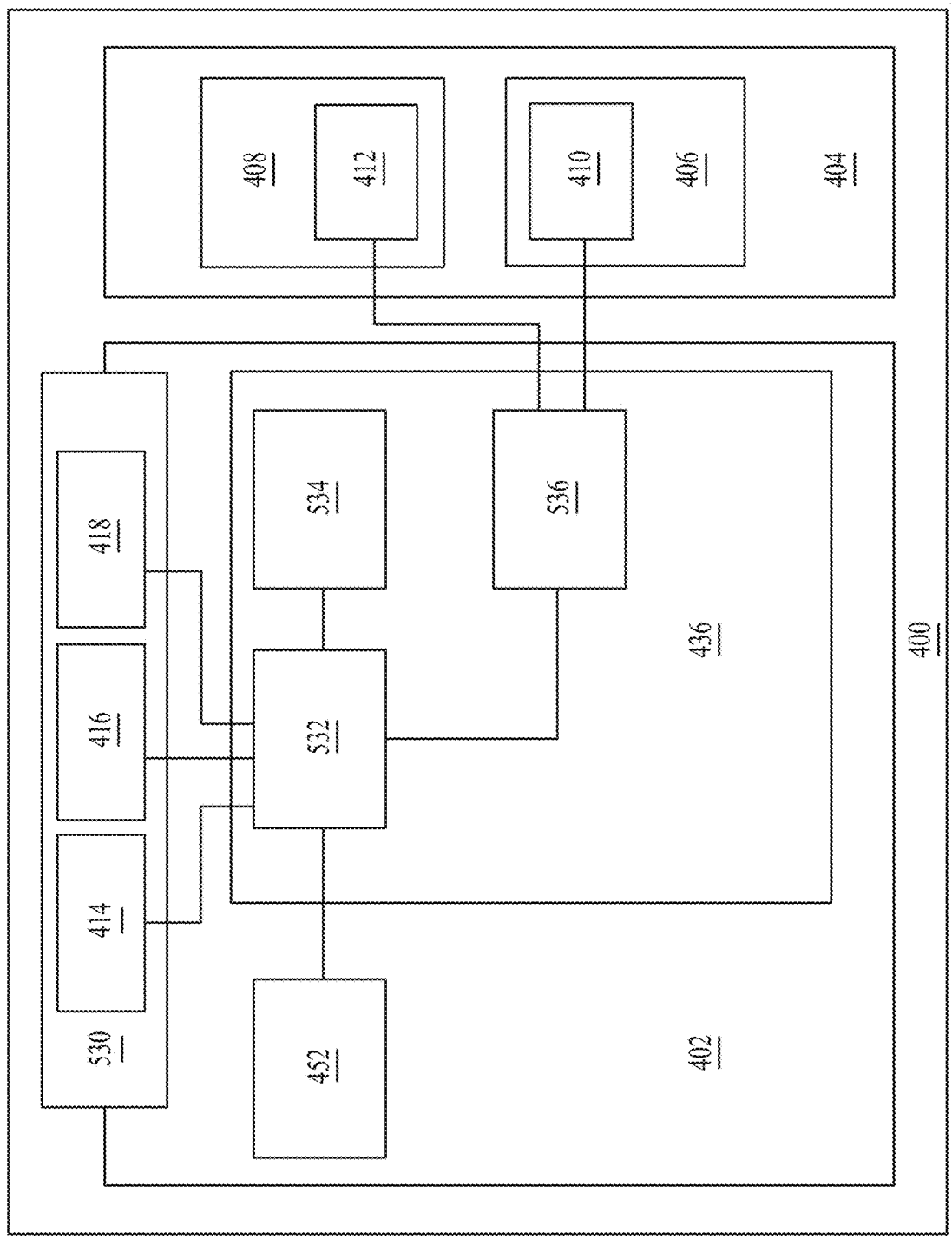
FIG. 5 shows a block diagram schematically representing a variation of a stimulator.

Generally, the systems used in the methods described herein may comprise a stimulator configured to deliver an electrical stimulus to the inner cavity of the nose. Some variations of the stimulation systems described here may comprise a handheld stimulator. FIGS. 4A, 4B, 4C, 4D, 4E show perspective, front, back, cut-away back, and cut-away side views, respectively, of an illustrative variation of a handheld stimulator 400, respectively. FIG. 5 shows a block diagram schematically representing the stimulator 400. As shown in FIGS. 4A-4E, the stimulator 400 may comprise a stimulator body 402 and a stimulator probe 404. Generally, the stimulator body 402 may be configured to generate a stimulus that may be delivered to the subject. The stimulator body 402 may comprise a front housing 438, back housing 440, and proximal housing 442, which may fit together to define a body cavity 454. The body cavity 454 may contain a control subsystem 436 and a power source 452, which together may generate and control the stimulus.

The stimulator body 402 may comprise a user interface 530 comprising one or more operating mechanisms to adjust one or more parameters of the stimulus. The operating mechanisms may provide information to the control subsystem 436, which may comprise a processor 532, memory 534, and/or stimulation subsystem 536. In some variations, the operating mechanisms may comprise first and second buttons 414 and 416. In some variations, pressing the first button 414 may turn on the stimulator and/or change one or more parameters of the stimulus (e.g., increase the intensity of the stimulus, change the stimulation pattern, or the like), while pressing the second button 416 may turn off the stimulator and/or change one or more parameters of the stimulus (e.g., decrease the intensity of the stimulus, change the stimulation pattern, or the like). Additionally or alternatively, the user interface may comprise one or more feedback elements (e.g., based on light, sound, vibration, or the like). As shown, the user feedback elements may comprise light-based indicators 418, which may provide information to the user.

In the variation shown in FIGS. 4A-4E, the user interface may be configured for use by the subject receiving the intranasal stimulation. However, in other variations, the stimulators may comprise an interface configured for use by a person other than the subject receiving the intranasal stimulation, such as a medical professional. For example, a stimulator may comprise a remote interface operable at a distance from the stimulator body. The remote interface may be connected to the stimulator body wirelessly or in a wired manner (e.g., via a cable). The remote interface may allow the stimulator to be turned on/off and or may be used to change one or more parameters of the stimulation. A remote interface may be desirable, for example, so a medical professional can adjust the stimulus parameters when intranasal stimulation is delivered at the medical professional's office. In some variations, the stimulators may be configured to be controlled by both the subject receiving the intranasal stimulation and another person (e.g., a medical professional). For example, a stimulator may comprise a user interface on the stimulator body, as shown in FIGS. 4A-4E, and a remote interface.

The stimulus may be delivered to a subject via the stimulator probe 404. In some variations the stimulator body 402 and stimulator probe 404 may be reversibly attachable. Some or all of the stimulator 400 may be disposable. For example, in some variations the stimulator body may be permanently attached to the stimulator probe, and the entire stimulator may be disposable. In other variations, one or more portions of the stimulator 400 may be reusable. For example, in variations where the stimulator probe 404 is releasably connected to the stimulator body 402, the stimulator body 402 may be reusable, and the stimulator probe 404 may be disposable and periodically replaced.

The stimulator probe 404 may comprise at least one nasal insertion prong, which may be configured to be at least partially inserted into the nasal cavity of a subject. In the handheld stimulator variation shown in FIGS. 4A-4E, the stimulator probe 404 may comprise two nasal insertion prongs 406 and 408. The stimulator probe 404 may further comprise ridges 420, which may allow the subject to more easily grip the probe 404. Each nasal insertion prong may comprise at least one electrode. As shown, the probe 404 may comprise a first electrode 410 on nasal insertion prong 406 and a second electrode 412 on nasal insertion prong 408. As shown in the cut-away view of the stimulator 400 in FIG. 4D, the electrodes 410 and 412 may be connected to leads 430 and 432 located within prongs 406 and 408, respectively. The leads 430 and 432 may in turn be connected to connectors 422 and 424, respectively. Connectors 422 and 424 may extend through lumens in the proximal housing 442, and may connect directly or indirectly to the control subsystem 436 and power source 452. As such, the electrical stimulus may travel from the control subsystem 436 through the connectors 422 and 424, through the leads 430 and 432, and through the electrodes 410 and 412.

Figure 6A:
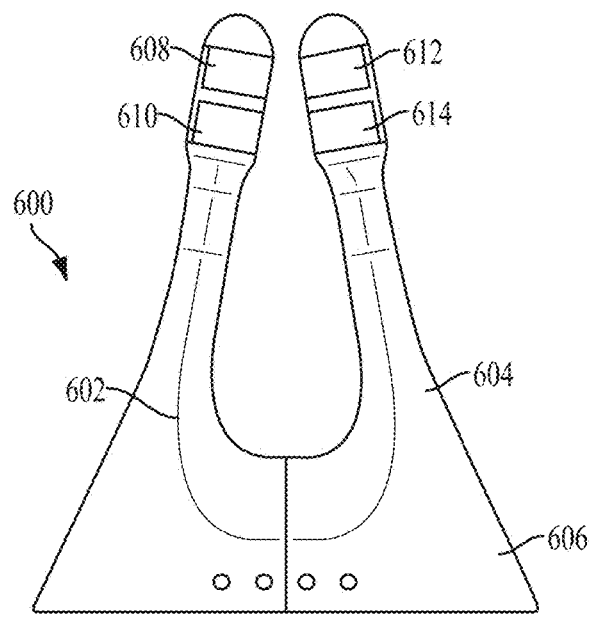
FIGS. 6A, 6B, and 6C depict back, front, and perspective views, respectively, of a stimulator probe suitable for the stimulators described here.
Figure 6B:
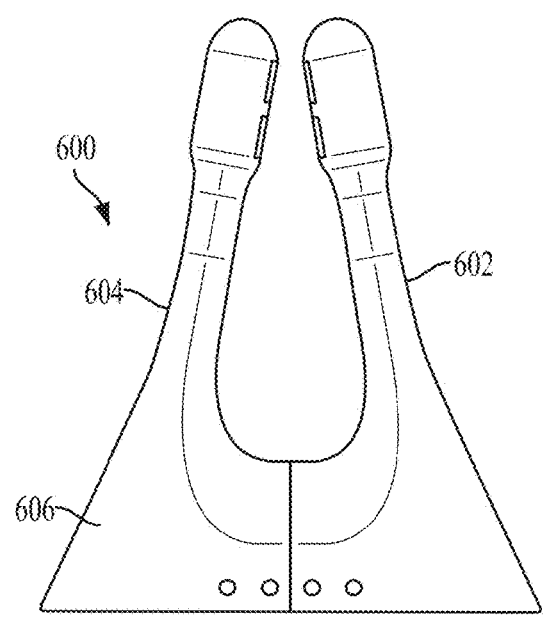
Figure 6C:
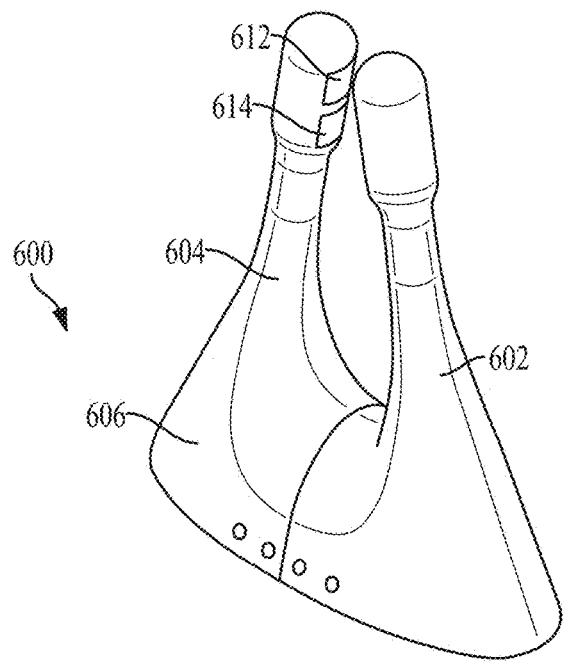

In some variations, the nasal insertion prongs may be parallel when not inserted into the nose of a subject, but may have sufficient flexibility to allow the prongs to self-align to the desired stimulation location when inserted into a user's nasal cavities. In other variations of stimulators comprising two nasal insertion prongs, however, the nasal insertion prongs may not be parallel to each other when not inserted into the nose of a subject; that is, the nasal insertion prongs may be positioned at an angle relative to each other. For example, FIGS. 6A-6C show a stimulator probe 600 comprising first and second nasal insertion prongs 602 and 604, respectively, connected to a base member 606. The nasal insertion prongs 602 and 604 may be connected to the base member 606 such that they are angled toward each other. In some variations, the angle between the nasal insertion prongs may be adjustable. For example, the nasal insertion prongs may be biased toward a configuration in which the nasal insertion prongs are at an angle relative to each other, but may be movable to a parallel configuration. When the prongs are inserted into nasal cavities to position tissue (e.g., a nasal septum) between the prongs, the prongs may be rotated away from each other (e.g., by application of a force) prior to insertion into the nasal cavities. Once positioned in the nasal cavities, the return bias may rotate the prongs toward each other (e.g., upon removal of the force), and the return bias of the stimulator probe may press the distal ends of the nasal insertion prongs against tissue. This may help to increase electrode apposition with tissue, and in some instances may act to hold the stimulator probe in place relative to tissue. To remove the stimulator probe from tissue, the prongs may again be rotated away from each other to release the tissue positioned between the prongs.

In some variations in which the stimulator comprises two nasal insertion prongs biased toward each other, the return bias may be sufficient to hold the stimulator in place. In these variations, once positioned in the nasal cavities, the distal ends of the nasal insertion prongs may press against tissue with sufficient force to allow for hands-free use—that is, the user may not need to hold the stimulator in order for the electrodes to remain in apposition with the target tissue. This may improve ease of use, particularly when stimulation is delivered for longer periods of time, as described in more detail herein. In other variations, the return bias may be sufficient to reduce unintended movement of the nasal insertion prongs while inserted, while still requiring the stimulator to be held.

The systems described herein may additionally or alternatively also comprise other features to allow hands-free or reduced-handling use. For example, the system may comprise a strap configured to be placed around a user's head and attached to the stimulator to hold the stimulator in place during stimulation. The strap may be removably attachable to the stimulator, or in other variations may be permanently attached to the stimulator. In some variations of stimulators configured for hands-free use, the stimulators may be configured to be inserted and/or removed by a user. In other variations, the stimulators may be configured to be inserted/removed by a medical professional.

Figure 7A:
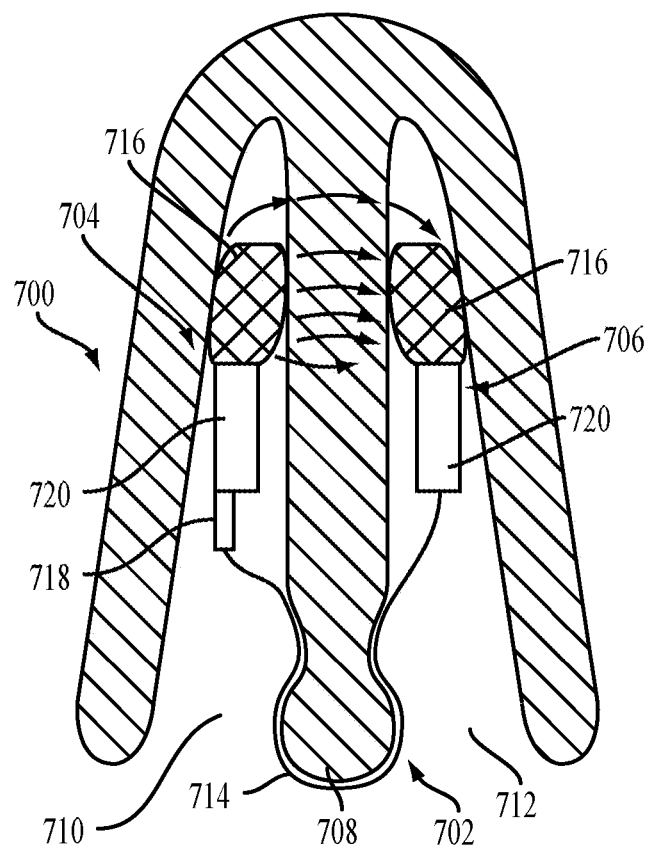
FIG. 7A shows a cross-sectional view of a stimulator positioned in the nasal cavities.

For example, FIG. 7 depicts a cross-sectional view of a subject's nose having a septum 708 and nostrils 710 and 712 having a variation of a hands-free stimulator 700 located therein. As shown there, the stimulator 700 may comprise a clip 702, a first stimulator unit 704 attached to a first end of the clip 702, and a second stimulator unit 706 attached to a second end of the clip 702. Generally, the clip 702 may be configured to temporarily connect the stimulator 700 to a nasal septum 708 of a subject, which may position the first stimulator unit 704 in the first nostril 710 and the second stimulator unit 706 in the second nostril 712.

In some variations, the clip 702 may comprise a u-shaped portion 714 configured to receive and clamp to a portion of the nasal septum 708. This engagement between the clip 702 and the nasal septum 708 may limit advancement of the stimulator 700 into the nose (e.g., to prevent over-insertion of the stimulator 700). The clip 702 may exert sufficient pressure on the septum 708 so as to resist removal of the stimulator 700 from the nose. Accordingly, the clip 702 may allow the stimulator to be positioned in the nose of a subject, and the subject may wear the stimulator without needing to actively hold the stimulator in the nose. The clip 702 may be removed by flexing the clip 702 to disengage it from the septum. As such, the subject may be able to insert and remove the stimulator 700 him- or herself. In some variations, the clip 702 may be at least partially formed from one or more shape memory materials (e.g., a nickel-titanium alloy), such that the clip 702 may be deformed to disengage the clip 702 from the septum 708 and may return to its original shape. In some variations an exterior portion of the clip 702 may be formed from one or more insulating materials (e.g., PTFE, silicone, combinations thereof, or the like), and an interior portion may include an electrically conductive core (e.g., a wire of any suitable metal, such as silver, stainless steel, platinum, alloys thereof, or the like) electrically connecting the first stimulator unit 704 to the second stimulator unit 706. In these variations, the insulating outer portion of the clip 702 may prevent inadvertent electrical stimulation between the clip 702 and the subject.

Generally, each stimulator unit may comprise one or more electrodes 716. In some variations, it may be desirable for the stimulator units to comprise a radially expandable structure that may expand to contact the nasal mucosa when inserted into the nostrils. While shown in FIG. 7 as being formed from an expandable wire mesh/braid electrode, each electrode 716 may be configured in any suitable manner. For example, in some variations the electrodes may comprise a hydrogel. Additionally or alternatively, it may be desirable for the stimulator units to comprise a smooth surface to prevent tissue abrasion. The stimulator may be configured such that the electrodes 716 are placed in contact with any suitable tissue structure or structures (e.g., the nasal mucosa above the columella, such as the nasal mucosa superior to the columella (e.g., the nasal mucosa near the interface between the nasal bone and the upper lateral cartilage) when the clip 702 is connected to the nasal septum.

Generally, the first 704 and/or second 706 stimulator units may comprise a housing 720, which may comprise a control subsystem having a processor, a stimulation subsystem, and a memory. In some variations the control subsystem may have a detection subsystem. Additionally or alternatively, the stimulator may comprise a communication subsystem. The stimulator circuitry may be housed in a single housing 720 (e.g., a housing 720 of the first stimulator unit 704 or a housing 720 of the second stimulator unit 706), or may be divided between multiple housings (e.g., a housing 720 of the first stimulator unit 704 and a housing 720 of the second stimulator unit 706). In some variations, the stimulator 700 may comprise a power source (e.g., a battery) (not shown). In other variations, the stimulator 700 may be powered wirelessly (e.g., via power received from a coil 718 or other antenna).

Figure 8B:
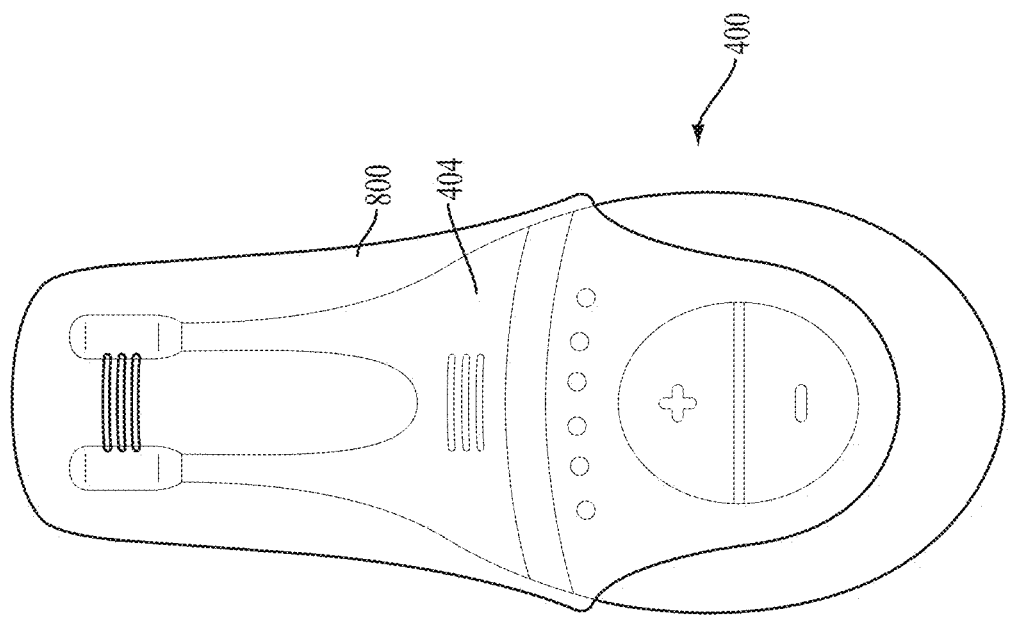
FIGS. 8A and 8B show perspective and front views, respectively, of the stimulator of FIGS. 4A-4E with an attached cap.
Figure 8A:
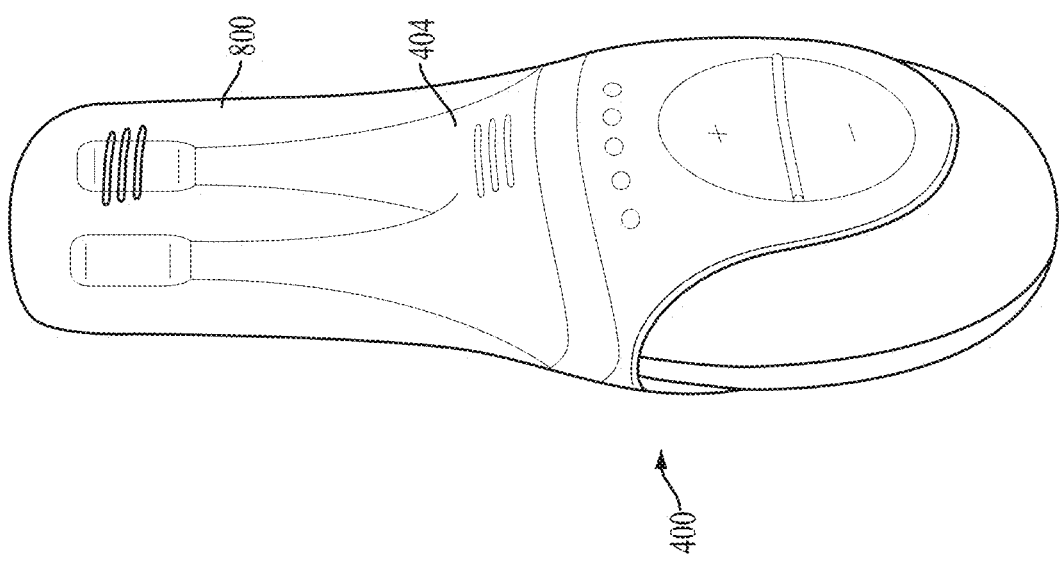
Figure 9C:
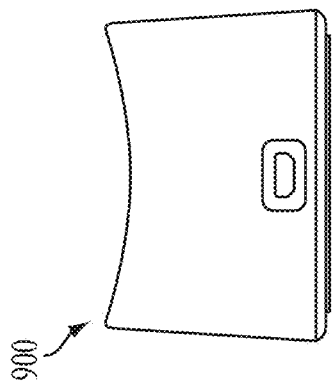
FIGS. 9A-9D depict portions of a stimulator system comprising a stimulator and a base station.
Figure 9D:
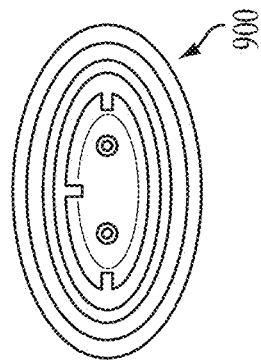
Figure 9B:
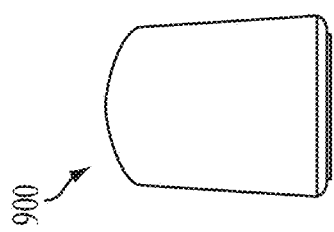
Figure 9A:
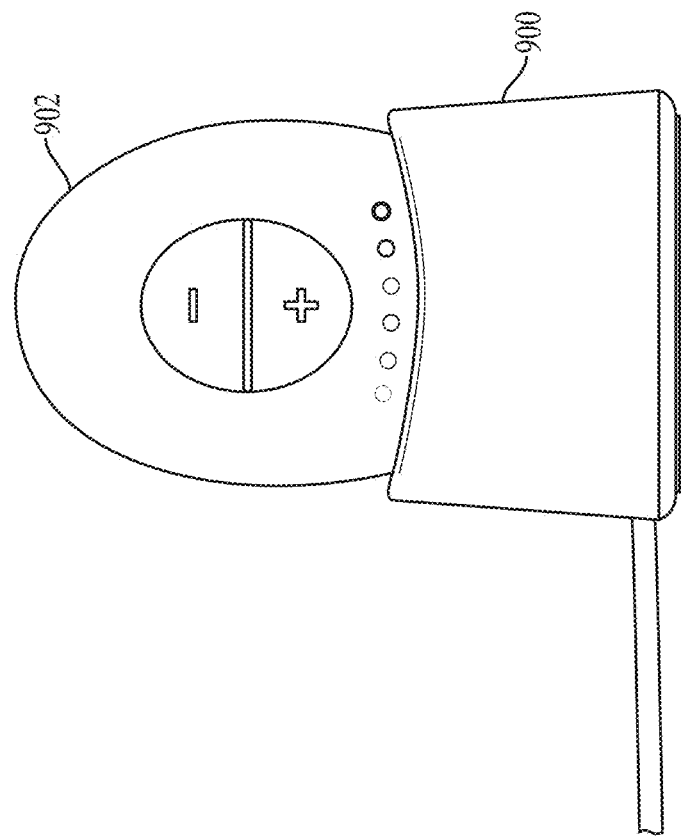

In some variations, the stimulators described here may comprise a cap to protect the stimulator probe. For example, FIGS. 8A and 8B show perspective and front views, respectively, of stimulator 400 with an attached cap 800. As shown there, the cap 800 may fit over the stimulator probe 404, which may protect the probe from contamination. More particularly, it may be desirable for the cap to protect the nasal insertion prongs, and especially the electrodes, from contamination. The systems described here may additionally or alternatively comprise a base station. The base station may be configured to releasably connect to one or more portions of the stimulator, and may be configured to perform one or more functions when connected to the stimulator. FIGS. 9A-9D depict a portion of a stimulator system comprising a base station 900 as described here. FIG. 9A shows a front view a stimulator body 902 docked in the base station 900, while FIGS. 9B, 9C, and 9D depict side, back, and top views of the base station 900, respectively. In variations where the stimulator body 902 comprises a rechargeable power source (such as a rechargeable battery, capacitor, or the like), the base station 900 may be configured to recharge the rechargeable power source.

Figure 7B:
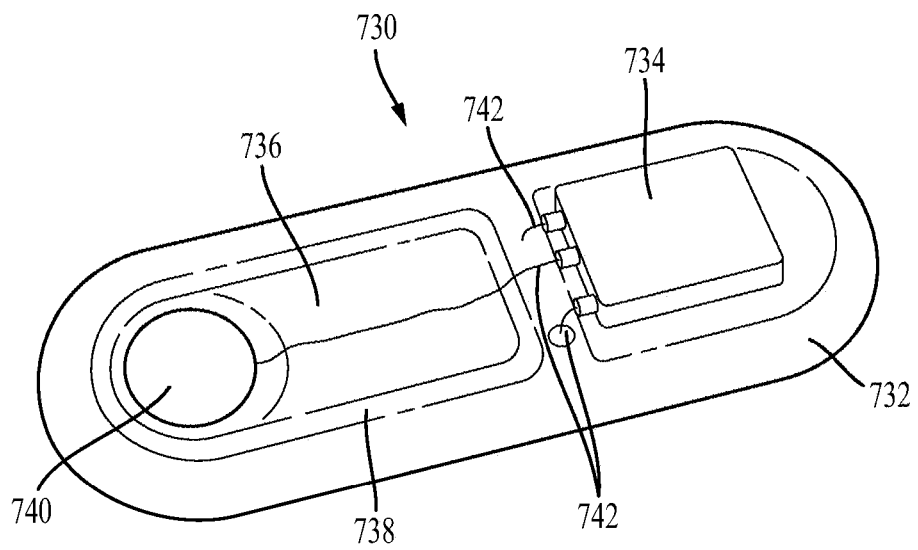
FIG. 7B shows a perspective view of a variation of an implantable microstimulator.

In other variations of stimulator systems suitable for use in the methods described herein, all or a portion of the systems may be surgically implantable. For example, FIG. 7B shows an implantable microstimulator 730. As shown, the microstimulator 730 may comprise a housing and an extension 736 connected to the housing. Generally, the microstimulator may be inserted into a tissue pocket within the nasal submucosal layer. The shape and size of the microstimulator may be flat and thin and may aid in atraumatic insertion of the device into nasal tissue. One or more portions of the microstimulator (e.g., an extension) may be formed from a flexible material such as silicone and/or may be a molded component, such as a molded silicone, which may allow the microstimulator to conform to one or more portions of the anatomy (e.g., the nasal septum) and/or prevent trauma during implantation. In some variations, the microstimulator may be encapsulated in a coating. A coating, such as silicone, may provide electrical insulation, waterproofing, biocompatibility, and/or safety (e.g., rounded edges, lubricious surface that slides easily over the nasal septum). FIG. 7B shows a variation of a microstimulator 730 encapsulated in a coating 732.

The microstimulator may be small enough to be inserted through a nostril and implanted within a layer of submucosa adjacent to the nasal septum or a turbinate without significantly interfering with the passage of air or fluid through the nasal cavity. In some variations the dimensions may be less than about 30 mm by about 10 mm by about 5 mm (L×W×H). In some of these variations, the dimensions may be about 15 mm-25 mm by about 3 mm-7 mm by about 1 mm-3 mm (L×W×H). In some of these variations, the dimensions may be about 17 mm by about 5 mm by about 2 mm (L×W×H).

The housing of the microstimulator 730 may comprise a housing case 734 containing some or all of a stimulation circuit. The housing case may be hermetically sealed and may be formed from one or more metals (e.g., titanium) or other biocompatible materials. In a microstimulator that comprises a passive stimulation circuit without an internal power source, the microstimulator may comprise one or more elements to receive power from an external source. For example, a controller may generate and transmit power wirelessly via an output signal (e.g., magnetic field). The microstimulator may comprise one or more energy-receiving units that receive the output signal from the controller to power the microstimulator. In some variations, the energy-receiving unit may be located in the extension of the microstimulator. The energy-receiving unit may be a coil, which may be formed from a wire having a length turned into a plurality of windings.

The extension of the microstimulator may comprise one or more electrodes, which may deliver an electrical stimulus to tissue. In FIG. 7B, the extension 736 comprises one electrode 740. However, it should be appreciated that the extension may comprise any suitable number of electrodes (e.g., one, two, three, or four or more electrodes) positioned on any suitable portion or portions of the extension. The microstimulator may comprise one or more feedthroughs that extend between and electrically connect the housing and the extension. For example, FIG. 7B illustrates feedthroughs 742, which extend between the housing case 734 and the extension 736, which may electrically connect the circuitry within the housing to the coil 738 and/or electrode 740 on the extension 736.

Systems comprising an implantable stimulator may comprise a controller, which may communicate with an implanted microstimulator to transmit and/or receive power, information, or the like. The controller may remain external to the body and communicate wirelessly with the microstimulator. In some variations, the output signal produced by the controller may provide power to the microstimulator. The controller may be brought into the vicinity of an implanted microstimulator, and may produce an output signal received by the implanted microstimulator. The implanted microstimulator may in turn generate a stimulation signal used to stimulate an anatomical target, as described in more detail herein. It should be appreciated that the controller may comprise any suitable form. For example, the controller may comprise a hand-held device. In other variations, the controller may comprise a wearable device (e.g., glasses, wristwatch), a key fob, or the like.

Other variations and features of stimulator systems and components thereof suitable for use in the methods described herein are described in U.S. application Ser. No. 14/256,915, filed Apr. 18, 2014, and titled "NASAL STIMULATION DEVICES AND METHODS"; in U.S. patent application Ser. No. 14/630,471, filed on Feb. 24, 2015, and titled "POLYMER FORMULATIONS FOR NASOLACRIMAL STIMULATION"; in U.S. patent application Ser. No. 14/920,860, filed Oct. 22, 2015, and titled "STIMULATION DEVICES AND METHODS FOR TREATING DRY EYE"; in U.S. patent application Ser. No. 14/920,852, filed Oct. 22, 2015, and titled "IMPLANTABLE NASAL STIMULATOR SYSTEMS AND METHODS"; and in U.S. patent application Ser. No. 14/809,109, filed Jul. 24, 2015, and titled "STIMULATION PATTERNS FOR TREATING DRY EYE," each of which is hereby incorporated by reference in its entirety.

In general, the stimulators may be programmed to deliver waveforms configured to generate rhythmical contraction and relaxation of the orbicularis muscle of the eyelid. In some variations, the waveforms may be pulse-based. The waveforms may be configured to stimulate tissue on both sides of the nose, or the waveforms may be configured to stimulate tissue on a single side of the nose. In some variations, the waveform may comprise symmetric biphasic pulses. The waveform may have any suitable parameters (e.g., frequency, pulse width, amplitude) in order to cause meibum expression or to otherwise cause rhythmical contraction and relaxation of the orbicularis muscle.

Generally, the stimulus may comprise a waveform of less than about 200 Hz. In some of these variations, the frequency is preferably between about 10 Hz and about 200 Hz. In some of these variations, the frequency is preferably between about 30 Hz and about 150 Hz. In others of these variations, the frequency is preferably between about 50 Hz and about 80 Hz. In others of these variations, the frequency is preferably between about 30 Hz and about 60 Hz. In others of these variations, the frequency is preferably between about 30 Hz and about 80 Hz. In some variations, the frequency may be about 1.5 Hz, about 10.25 Hz, about 70 Hz, about 150 Hz, about 25 Hz, about 27.5 Hz, about 30 Hz, about 32.5 Hz, about 35 Hz, about 37.5 Hz, about 40 Hz, about 42.5 Hz, about 45 Hz, about 47.5 Hz, about 50 Hz, about 52.5 Hz, about 55 Hz, about 57.5 Hz, about 60 Hz, about 62.5 Hz, or about 65 Hz. In some variations, the frequency of the waveform may vary over time.

Generally, when the stimulus comprises a biphasic pulse and the first phase of the biphasic pulse is current-controlled, the first phase may preferably have an amplitude between about 1.0 mA and about 10 mA. Amplitudes within these ranges may be high enough to stimulate targeted tissue, but sufficiently low as to avoid any significant heating of tissue, ablation of tissue, or the like. In some variations the amplitude may be between about 1.0 mA and about 5.0 mA. In other variations, the first phase may have an amplitude of about 0.1 mA, about 0.2 mA, about 0.3 mA, about 0.4 mA, about 0.5 mA, about 0.6 mA, about 0.7 mA, about 0.8 mA, about 0.9 mA, or about 1.0 mA. In some variations, the amplitude may be variable. For example, the amplitude may vary between about 1.3 mA and about 1.5 mA, about 2.2 mA and about 2.5 mA, about 3.2 mA and about 3.7 mA, or about 4.3 mA and about 5.0 mA. When the first phase of a biphasic pulse is voltage-controlled, the first phase may preferably have an amplitude between about 10 mV and about 100 V.

Figure 10A:
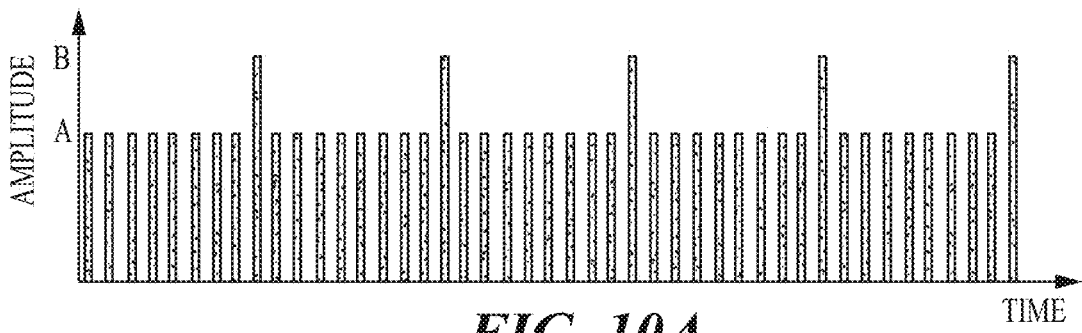
FIGS. 10A-10D illustrate exemplary amplitude modulation of waveform parameters.
Figure 10B:
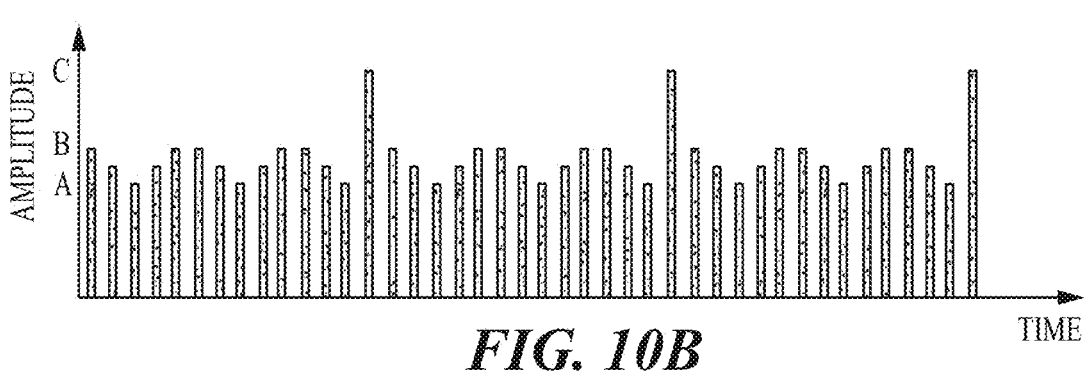
Figure 10C:
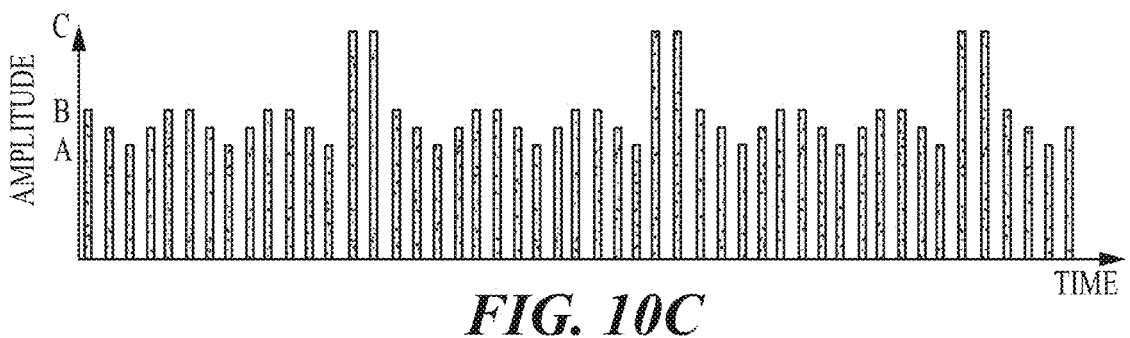
Figure 10D:
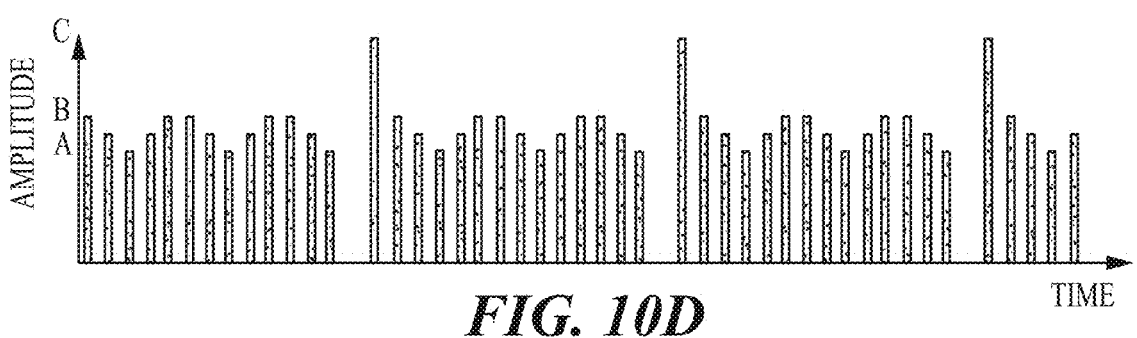

When a stimulator is configured to deliver a pulse-based waveform, in some variations, the amplitude of the pulses may be constant over time. In other variations, the amplitude of the pulses may vary over time. This may reduce subject accommodation. In some variations, the amplitude of pulses may increase (linearly, exponentially, etc.) from a minimum value to a maximum value, drop to the minimum value, and repeat as necessary. In some variations, the amplitude of the pulses may vary according to a sinusoidal profile. In another variation, as illustrated in FIG. 10A, the amplitude may periodically increase from a baseline amplitude (A) to a higher amplitude (B) for a single pulse. In yet another variation, as illustrated in FIGS. 10B-10C, the amplitude of the pulses may follow a periodically increasing and decreasing pattern between two lower amplitudes (A, B), and periodically increase to a higher amplitude (C) for a single pulse (FIG. 10B) or for a plurality of pulses (e.g., two pulses) (FIG. 10C). In yet another variation, as illustrated in FIG. 10D, a higher amplitude pulse (or pulses) may be preceded by a brief pause (i.e., no current delivery). Each of these types of amplitude modulation may be implemented alone or in combination with any other type of amplitude modulation, and may reduce subject accommodation.

In some variations in which the amplitude varies over time, the amplitude may vary at a frequency suitable for reducing subject accommodation or increasing subject comfort, such as between about 0.1 Hz and about 5 Hz, between about 1 Hz and about 5 Hz, between about 1 Hz and about 2 Hz, between about 2 Hz and about 3 Hz, between about 3 Hz and about 4 Hz, or between about 4 Hz and about 5 Hz. In some variations, the amplitude may vary at a frequency of about 1.0 Hz, about 1.1 Hz, about 1.2 Hz, about 1.3 Hz, about 1.4 Hz, about 1.5 Hz, about 1.6 Hz, about 1.7 Hz, about 1.8 Hz, about 1.9 Hz, about 2.0 Hz, about 2.1 Hz, about 2.2 Hz, about 2.3 Hz, about 2.4 Hz, about 2.5 Hz, about 2.6 Hz, about 2.7 Hz, about 2.8 Hz, about 2.9 Hz, about 3.0 Hz, about 3.1 Hz, about 3.2 Hz, about 3.3 Hz about 3.4 Hz, about 3.5 Hz, about 3.6 Hz, about 3.7 Hz, about 3.8 Hz, about 3.9 Hz, or about 4.0 Hz. In some variations, it may be desirable for the amplitude to vary at a frequency suitable for achieving a "pumping" action that may help to express meibum and open blocked meibomian glands. In other variations, the stimulation waveform may be a modulated high frequency signal (e.g., sinusoidal), which may be modulated at a beat frequency of the ranges described above. In such variations, the carrier frequency may be between about 100 Hz and about 100 kHz.

When the stimulus comprises a biphasic pulse, the first phase may preferably have a pulse width between about 1 μs and about 10 ms. In some of these variations, the pulse width may be between about 10 μs and about 100 μs. In other variations, the pulse width may be between about 100 μs and about 1 ms. In yet other variations, the pulse width may be between about 0 μs and about 300 μs. In yet other variations, the pulse width may be between about 0 μs and 500 μs. It may be desirable to have a longer pulse width to achieve a "pumping" action that may help to express meibum and open blocked meibomian glands.

Figure 11A:
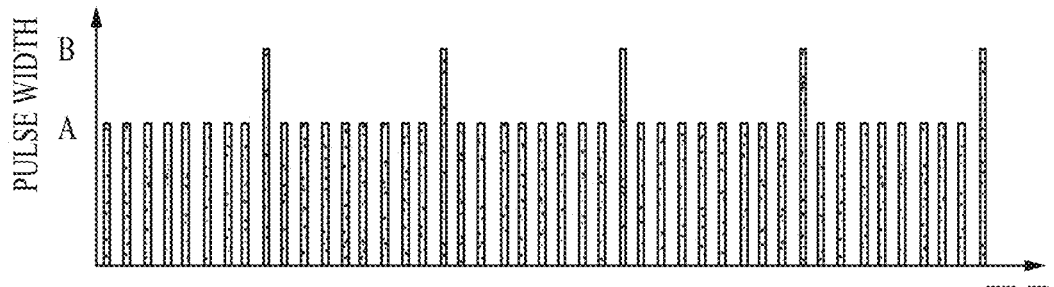
FIGS. 11A-11D and 12 illustrate exemplary pulse width modulations.
Figure 11B:
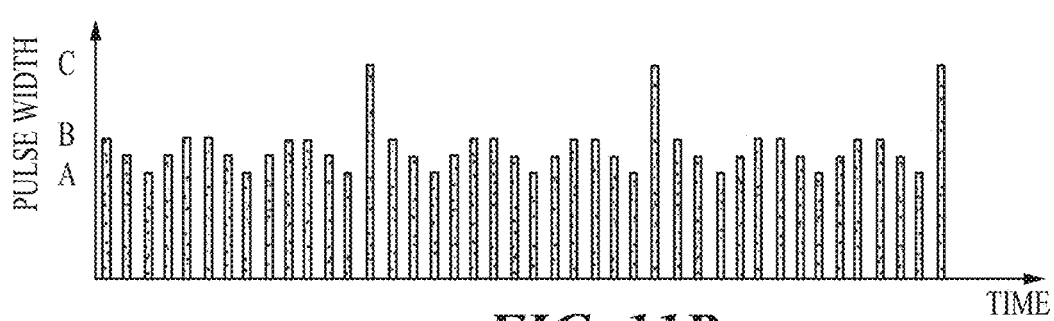
Figure 11C:
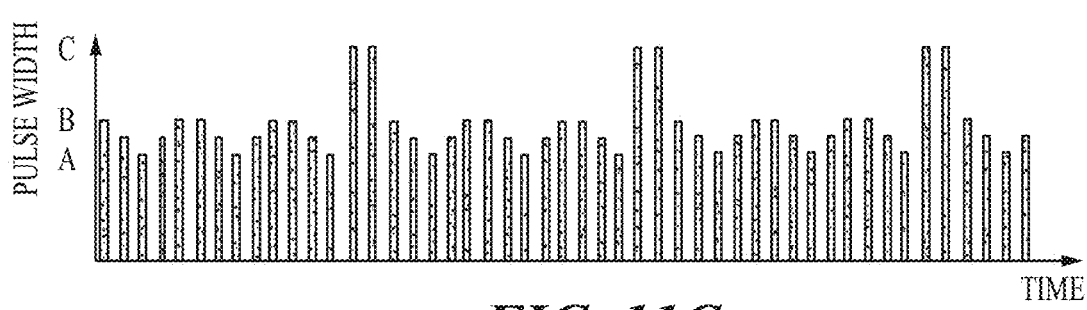
Figure 11D:
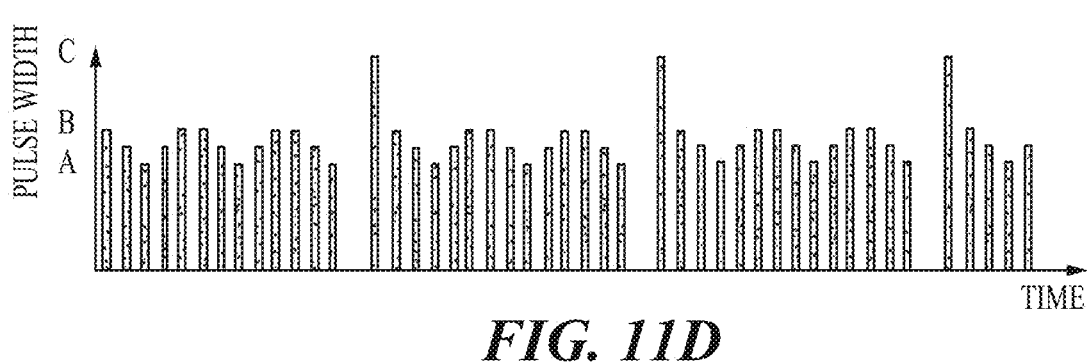

In some variations, the pulse width may be constant over time. In other variations, the pulse width may vary over time. Pulse width modulation over time may increase the efficacy and/or comfort of the stimulation. In some variations, the pulse width may increase (linearly, exponentially, etc.) from a minimum value to a maximum value, drop to the minimum value, and repeat as necessary. In some variations, the pulse width may vary according to a sinusoidal profile. In another variation, as illustrated in FIG. 11A, the pulse width may periodically increase from a baseline pulse width (A) to a longer pulse width (B) for a single pulse. In yet another variation, as illustrated in FIGS. 11B-11C, the pulse width may follow a periodically increasing and decreasing pattern between two shorter pulse widths (A, B), and periodically lengthen to a longer pulse width (C) for a single pulse (FIG. 11B) or for a plurality of pulses (e.g., two pulses) (FIG. 11C). In yet another variation, as illustrated in FIG. 11D, a longer pulse width pulse (or pulses) may be preceded by a brief pause (i.e., no current delivery). Each of these types of pulse width modulation may be implemented alone or in combination with any other type of pulse width modulation. In any form of pulse width modulation, the pulse width may vary at any suitable frequency. In some variations the pulse width may vary at about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 1.1 Hz, about 1.2 Hz, about 1.3 Hz, about 1.4 Hz, or about 1.5 Hz. In some variations, modulation of the pulse width at a rate between about 0.5 Hz and 1 Hz may be desirable to increase subject comfort during stimulation.

In some variations, the increase and decrease of pulse width may be defined by a function implemented by the stimulator. For example, the pulse width may be defined by a function such that the pulse width varies exponentially. In one variation, the function defining pulse width may comprise two phases—a first phase during which the pulse width of the leading pulse increases over time, and a second phase during which the pulse width of the leading pulse decreases over time. During the first phase, the pulse width of the leading pulse approaches the maximum pulse width according to an exponential function, where at time t, PW{t} is defined by the equation $$PW\{t\} = (PW_{max} - PW_{min})\left(1 - e^{-\left(\frac{t}{\tau}\right)}\right)$$

where $PW_{max}$ is the maximum allowed pulse width, $PW_{min}$ is the minimum allowed pulse width, and τ is a time constant.

Once a predetermined amount of time has elapsed (a multiple of time constant τ), the pulse width modulation may enter the second phase. During the second phase, the pulse width of the leading pulse exponentially decays from its maximum value to a minimum value following the exponential equation $$PW\{t\} = (PW_{max} - PW_{min})\left(e^{-\left(\frac{t}{\tau}\right)}\right).$$

After a predetermined amount of time has elapsed (a multiple of time constant τ), the pulse width modulation may re-enter the first phase, and the cycle may repeat. The pulse width of the secondary (charge balancing) pulse is increased and decreased accordingly to retain charge full balancing. $PW_{max}$, $PW_{min}$, and τ may have any suitable values to achieve the pulse widths described herein, but in one example the waveform may have a $PW_{max}$ of 300 μs, $PW_{min}$ of 0 μs, and τ of ⅓ μs. In other variations, for example, $PW_{max}$ may be about 100 μs, about 200 μs, about 300 μs, about 400 μs, or about 500 μs; $PW_{min}$ may be about 0 μs, about 10 μs, about 50 μs, or about 100 μs; and τ may be about ⅓ μs, about ¼ μs, about ⅕ μs, or about ⅙ μs. An exemplary function defining exponentially increasing and decaying pulse widths is shown in FIG. 12.

In some instances, the waveforms may be delivered in a continuous fashion, while in other instances, the waveforms may be delivered in a non-continuous fashion having on periods and off periods. Exemplary on/off durations include without limitation, 0.5 seconds on/0.5 seconds off, 1 second on/1 second off, 1 second on/2 seconds off, 2 seconds on/1 seconds off, 2 seconds on/2 seconds off, 5 seconds on/5 seconds off, 0.2 seconds on/0.8 seconds off, and less than 1 second on/less than 10 seconds off. Non-continuous delivery with on and off periods may help to reduce subject accommodation, may allow for rest periods for eyelid muscles caused to contract by afferent neurostimulation, and/or may be more effective than continuous delivery in causing meibum secretion onto the eyelids or dislocating meibum plugs at the gland openings.

Figure 12:
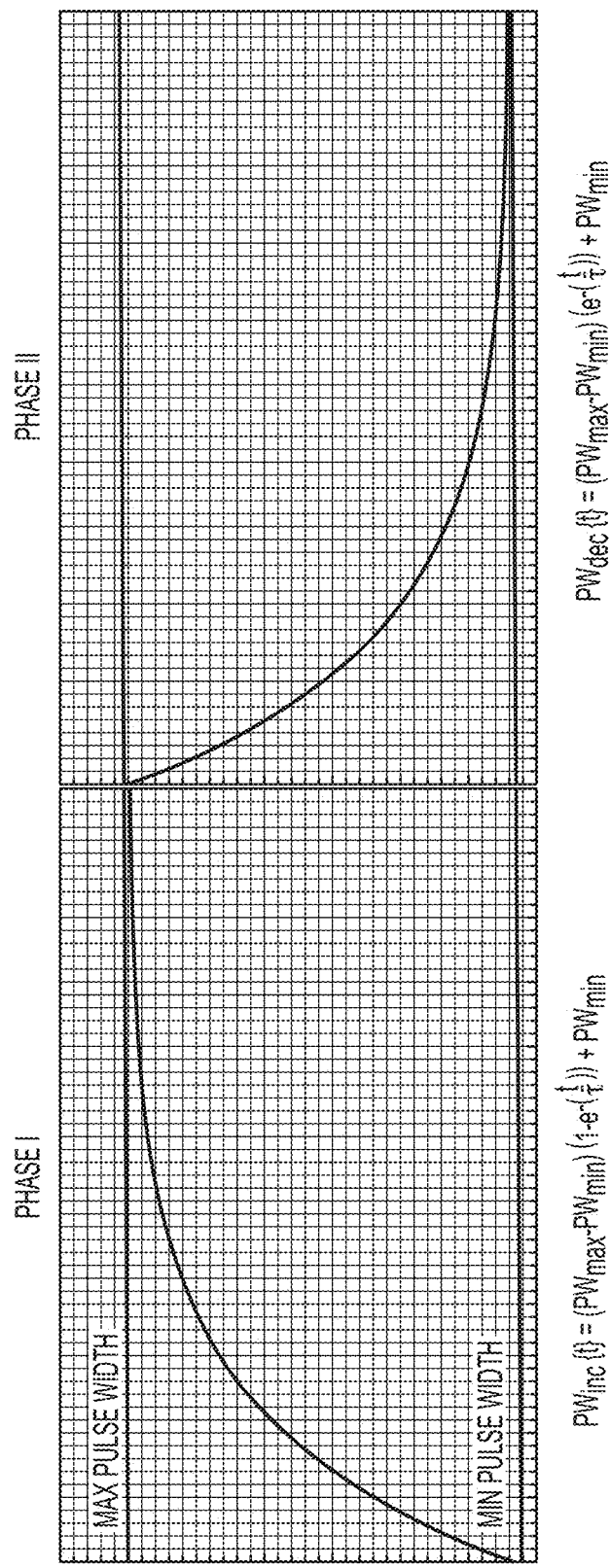
Figure 16A:
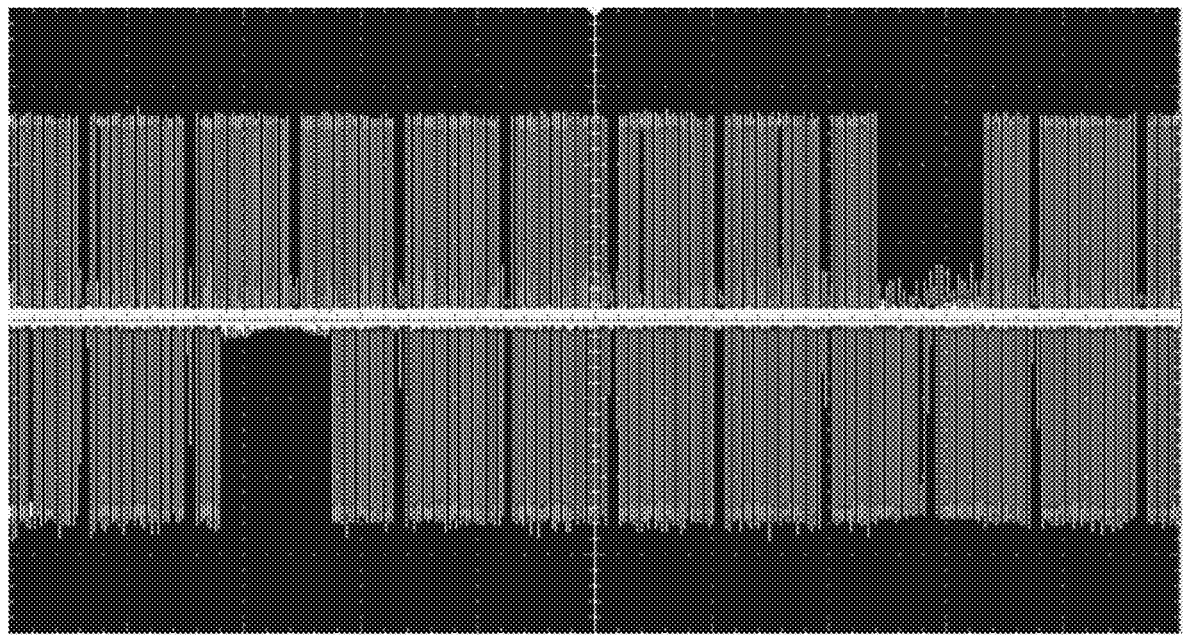
FIGS. 16A-16E depict exemplary waveforms showing multiple parameters that are concurrently modulated over time.

In one exemplary waveform, illustrated in FIG. 16A, the waveform may have a stimulation frequency of 30 Hz; a minimum stimulation current amplitude of 0.7 mA, a maximum stimulation current amplitude of 0.7 mA, and thus no variation in maximum stimulation current amplitude; a minimum pulse width of 0 µs; a maximum pulse width of 300 µs; a pulse width modulation frequency of 1 Hz (rising and falling according to an exponential function, as shown in FIG. 12); a minimum charge injection per phase (at 0 µs pulse width) of 0 µC; and a maximum charge injection per phase (at 0.7 mA and 300 µs) of 0.21 µC.

Figure 17:
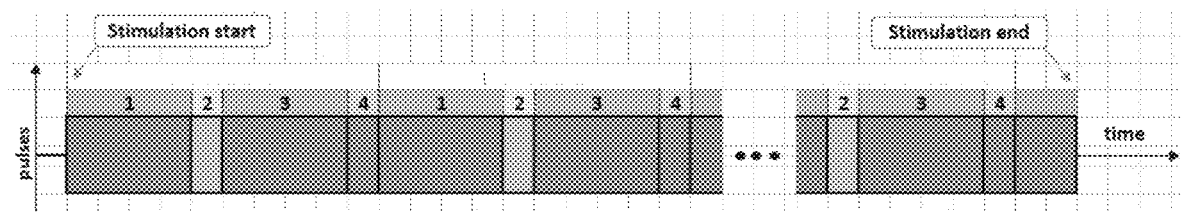
FIG. 17 illustrates exemplary shape modulation.

The waveform illustrated in FIG. 16A may have a pulse shape that is cycled between four periods, as shown in FIG. 17. The first period may comprise a two-phase current-controlled waveform with symmetrical phases. The second period may comprise a current-controlled first phase, followed by a voltage-controlled second phase. The first phase may have a current sourced by a first electrode and sunk by a second electrode, while the second phase may have a current sourced by the second electrode and sunk by the first electrode. The third period may comprise a two-phase current-controlled waveform with symmetrical phases (i.e., the third period may be the same as the first period). The fourth period may comprise a current-controlled first phase, followed by a voltage-controlled second phase. The first phase may have a current sourced by the second electrode and sunk by the first electrode, while the second phase may have a current sourced by the first electrode and sunk by the second electrode. In each period, the pulses may be charged-balanced.

The cycling of the waveform shape through different periods may sequentially preferentially stimulate a location closer to one electrode or the other. By doing so, the stimulation may favor the ipsilateral reflex pathway over the contralateral reflex pathway, thus having a greater effect on the orbicularis muscle on the ipsilateral side, while allowing the orbicularis muscle on the contralateral side to relax. The result may be a "pumping" action that may help to express meibum and open blocked meibomian glands. It may be desirable to have a sufficiently long duration for each period to cause this pumping action, such as but not limited to about 2 seconds, about 3 seconds, about 5 seconds, or about 10 seconds.

Figure 16B:
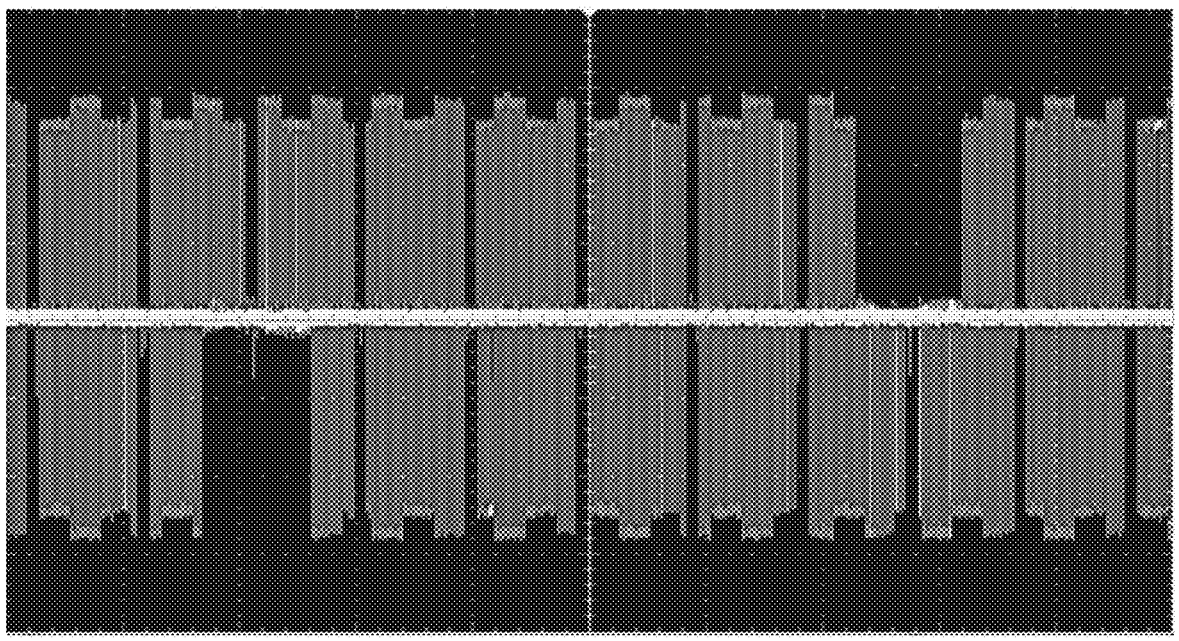

In another exemplary waveform, illustrated in FIG. 16B, the waveform may have a stimulation frequency of 37.5 Hz; a minimum stimulation current amplitude of 1.33 mA, a maximum stimulation current amplitude of 1.5 mA, a variation in maximum stimulation current amplitude of 0.17 mA, and an amplitude modulation frequency of 2.1 Hz; a minimum pulse width of 0 µs; a maximum pulse width of 300 µs; a pulse width modulation frequency of 1 Hz (rising and falling according to an exponential function, as shown in FIG. 12); a minimum charge injection per phase (at 0 µs pulse width) of 0 µC; a maximum charge injection per phase (at 1.5 mA and 300 µs) of 0.45 µC; and a pulse shape that is modulated as described above and shown in FIG. 17.

Figure 16C:
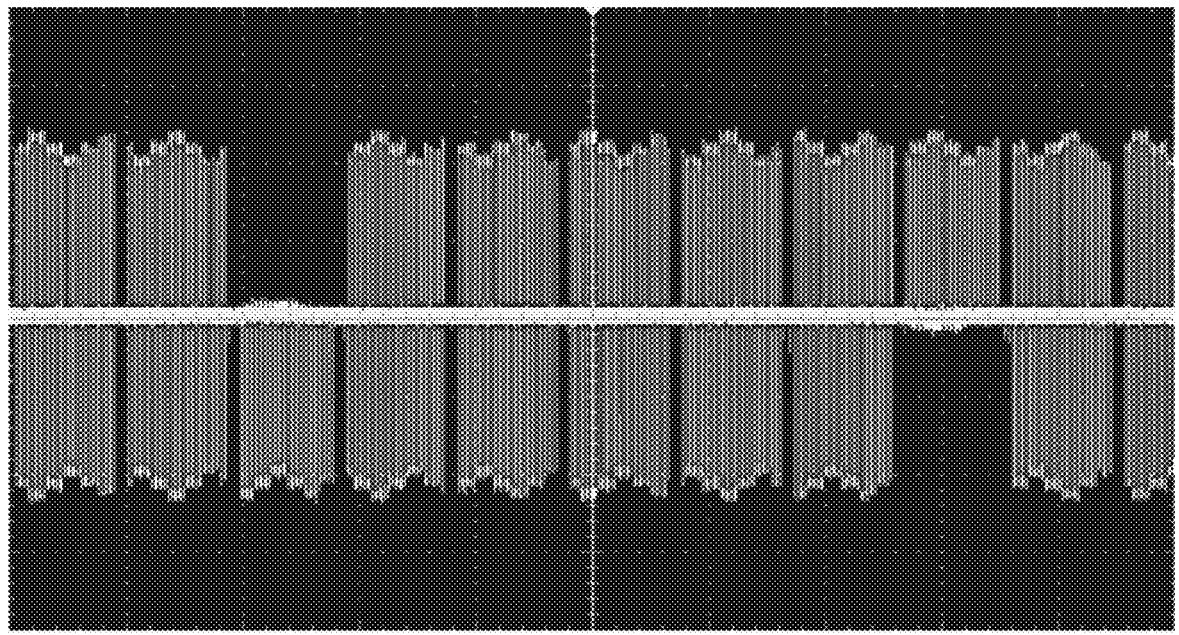

In another exemplary waveform, illustrated in FIG. 16C, the waveform may have a stimulation frequency of 45 Hz; a minimum stimulation current amplitude of 2.17 mA, a maximum stimulation current amplitude of 2.5 mA, a variation in maximum stimulation current amplitude of 0.33 mA, and an amplitude modulation frequency of 2.6 Hz; a minimum pulse width of 0 µs; a maximum pulse width of 300 µs; a pulse width modulation frequency of 1 Hz (rising and falling according to an exponential function, as shown in FIG. 12); a minimum charge injection per phase (at 0 µs pulse width) of 0 µC; a maximum charge injection per phase (at 2.5 mA and 300 µs) of 0.75 µC; and a pulse shape that is modulated as described above and shown in FIG. 17.

Figure 16D:
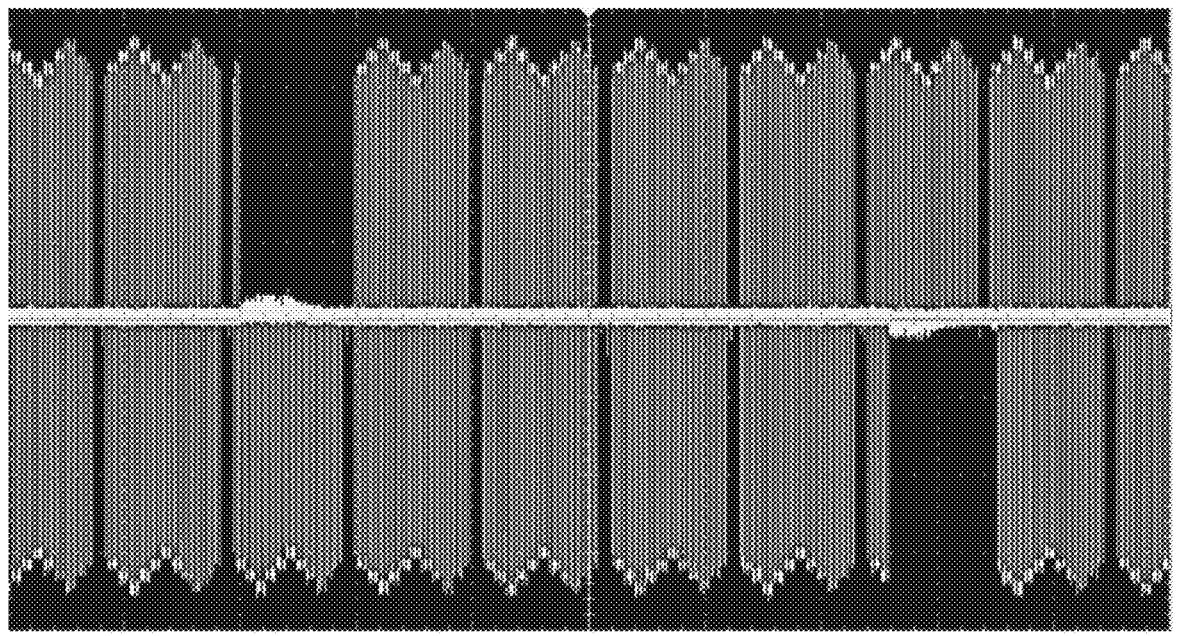

In another exemplary waveform, illustrated in FIG. 16D, the waveform may have a stimulation frequency of 52.5 Hz; a minimum stimulation current amplitude of 3.2 mA, a maximum stimulation current amplitude of 3.7 mA, a variation in maximum stimulation current amplitude of 0.5 mA, and an amplitude modulation frequency of 2.8 Hz; a minimum pulse width of 0 µs; a maximum pulse width of 300 µs; a pulse width modulation frequency of 1 Hz (rising and falling according to an exponential function, as shown in FIG. 12); a minimum charge injection per phase (at 0 µs pulse width) of 0 µC; a maximum charge injection per phase (at 3.7 mA and 300 µs) of 1.11 µC; and a pulse shape that is modulated as described above and shown in FIG. 17.

Figure 16E:
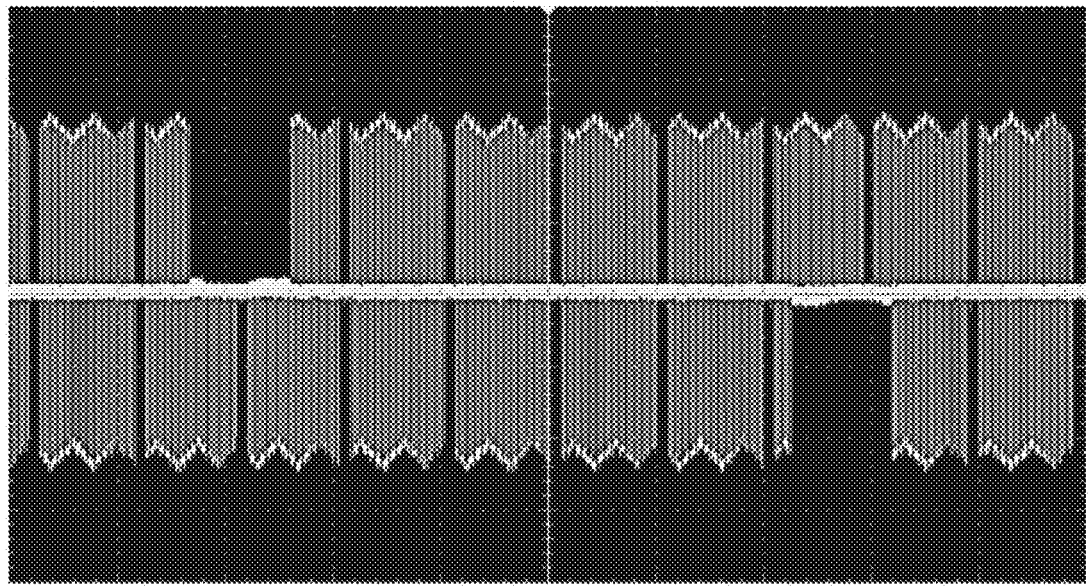

In another exemplary waveform, illustrated in FIG. 16E, the waveform may have a stimulation frequency of 60 Hz; a minimum stimulation current amplitude of 4.3 mA, a maximum stimulation current amplitude of 5.0 mA, a variation in maximum stimulation current amplitude of 0.67 mA, and an amplitude modulation frequency of 2.5 Hz; a minimum pulse width of 0 µs; a maximum pulse width of 300 µs; a pulse width modulation frequency of 1 Hz (rising and falling according to an exponential function, as shown in FIG. 12); a minimum charge injection per phase (at 0 µs pulse width) of 0 µC; a maximum charge injection per phase (at 5.0 mA and 300 µs) of 1.5 µC; and a pulse shape that is modulated as described above and shown in FIG. 17.

In some variations, the stimulators described herein may be configured to deliver current between different three or more stimulation contacts (e.g., electrodes) in order to allow for spatial patterning of the current delivery. In these cases, it may be desirable to apply two or more different waveforms between different stimulation contacts. Generally, it may be desirable to temporally or spatially pattern the stimulation in order to reduce accommodation over the longer stimulation times that may be used to treat meibomian gland disease/dysfunction and/or blepharitis. Exemplary waveforms and methods for reducing accommodation are described in U.S. application Ser. No. 14/920,860, filed Oct. 22, 2015, and titled "STIMULATION DEVICES AND METHODS FOR TREATING DRY EYE" and in U.S. patent application Ser. No. 14/809,109, filed Jul. 24, 2015, and titled "STIMULATION PATTERNS FOR TREATING DRY EYE," each of which was previously incorporated by reference in its entirety.

It may also be desirable to use waveforms that reduce sneezing during delivery. Sneezing may be particularly uncomfortable for a subject when intranasal electrical stimulation is delivered for longer durations, as it may be for treatment of meibomian gland disease/dysfunction and/or blepharitis. Certain waveform parameters that may reduce sneezing may include, for example, amplitude or pulse width ramps, pauses between portions of the waveform configured to preferentially stimulate the left and right sides of the nose, and/or using automated feedback (e.g., using an electromyogram (EMG) signal, as described in more detail herein) to determine when a patient may be about to sneeze. Just before a patient is about to sneeze, the waveform amplitude may be significantly reduced (unilaterally or bilaterally), or the amplitude or pulse width may be significantly increased to interrupt the sensation. Other techniques may include more pauses within the waveform, random pauses within the waveform, and/or amplitude or pulse width spikes.

Some variations of the methods described herein may comprise adjusting the waveform parameters based on feedback. In some variations the feedback may help to adjust the stimulus to be maximally effective in causing meibum secretion. Additionally or alternatively, the feedback may help to adjust the stimulus to prevent accommodation while limiting unpleasant sensations, such as a feeling of needing to sneeze. Such adjustment may make stimulation for a longer duration (e.g., five to ten minutes) more comfortable for a subject without resulting in subject accommodation.

In variations of methods comprising an in-office treatment component and an at-home treatment component, as described in more detail herein, different waveforms may be used for in-office and at-home stimulation. When different stimulators are used for in-office and at-home stimulation, a stimulator for in-office use may be programmed with a first set of waveforms, and a stimulator for at-home stimulation may be programmed with a second set of waveforms. Generally, the waveforms used for in-office stimulation may generate a stronger sensation than the waveforms use for at-home stimulation. For example, the waveforms used for in-office stimulation may have higher maximum amplitudes and longer on/off periods.

Methods

Generally, the stimulators described herein may be used to deliver intranasal stimulation to treat meibomian gland disease/dysfunction. The methods may comprise delivering intranasal stimulation to open obstructed portions of the meibomian glands or openings, causing acute expression of meibum from the glands, contributing to sustained increases in the quantity of meibum secretion (and thus sustained increases in the lipid content of tears), and/or contributing to sustained improvements in the quality of secreted meibum. It should also be appreciated that the methods described herein may be used as a prophylactic measure to treat users who may be at an increased risk of developing meibomian gland disease/dysfunction.

The stimulation may be delivered to the nasal mucosa. In some instances, the targeted area may comprise tissue innervated by the anterior ethmoidal branch of the nasociliary nerve. In some instances, the targeted area of the nasal mucosa may be superior to the columella. It may in some instances be near the inferior end of the nasal bone (i.e., near the interface between the nasal bone and the upper lateral cartilage). As such, the stimulus may be delivered between about 20 mm and about 35 mm into the nasal cavity of the patient, in some cases via an electrode between about 25 mm and about 35 mm into the nasal cavity of the patient. In other instances, the targeted area may be the columella. It may be desirable that the stimulus be delivered in the anterior portion of the nasal cavity, within the nostrils and anterior to the turbinates, and in some instances, at a location anterior to the middle turbinate, or at a location anterior to the inferior turbinate. The stimulus may be delivered at least partially through tissue of or near the septum, and it may in some instances be desirable to direct the stimulus such that a portion is directed toward the front of the nose. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth, and which may reduce rhinorrhea. It may also in some instances be desirable to direct the stimulus so as to reduce negative side effects that may occur from stimulation of the olfactory area.

The methods described herein may comprise delivering intranasal stimulation according to one or more treatment regimens. The methods described herein may also include determining a type of dry eye in a subject. The one or more treatment regimens may be selected based on the determined type of dry eye. For example, the methods may comprise determining that a subject afflicted with dry eye has meibomian gland disease/dysfunction. The methods may further comprise intranasally delivering or instructing a subject to deliver an electrical stimulation to the subject, where the intranasally delivered electrical stimulation is effective to treat meibomian gland disease/dysfunction. For example, to treat meibomian gland disease/dysfunction, stimulation may be delivered to a subject as needed and/or according to a predetermined plan. In some variations, it may be desirable that each round of stimulation is long enough to result in acute meibum secretion. It may in some instances take several or more minutes of intranasal stimulation to achieve meibum secretion, depending on the severity of meibomian gland disease/dysfunction. For example, in a patient with severe meibomian gland disease/dysfunction, it may take about 5 to 10 minutes to achieve meibum secretion, while in a patient with moderate meibomian gland disease/dysfunction, it may take about 3 to 5 minutes to achieve meibum secretion, while in a patient without meibomian gland disease/dysfunction, it may take only about 1 minute to achieve meibum secretion with particular stimulus parameters.

In some variations, the methods described herein may comprise repeated delivery of intranasal electrical stimulation over an extended period of time, such as but not limited to at least 30 days, at least 45 days, at least 60 days, or at least 90 days. For example, the method may comprise daily delivery of intranasal electrical stimulation over an extended period of time, such as but not limited to at least 30 days, at least 45 days, at least 60 days, or at least 90 days.

In some variations, the methods described herein may comprise an initial round of stimulation that is longer than subsequent rounds of stimulation. The initial round of stimulation may in some variations be of a length sufficient to achieve meibum secretion in a patient with meibomian gland disease/dysfunction who has not previously been treated with electrical intranasal stimulation. Because the openings or other portions of these patients' meibomian glands may be significantly obstructed, a longer stimulation duration may be needed to achieve meibum expression. As described in more detail herein, intranasal stimulation may cause massaging of the meibomian gland due to contractions of eyelid muscles, and may cause warming of the meibomian glands, which may loosen and reduce the viscosity of meibum and ultimately allow meibum to be secreted onto the eyelid margin; however, in a patient with significantly obstructed meibomian glands, longer stimulation may be needed to achieve a noticeable effect. For example, an initial round of stimulation may have a duration of between about 5 and 10 minutes. In some of these variations, an initial round of stimulation may have a duration of between about 5 and 7 minutes, between about 7 and 10 minutes, or between about 7 and 8 minutes.

Subsequent rounds of stimulation after an initial round of stimulation may be shorter, for example, about 1 to 3 minutes. These subsequent rounds may not need to be as long as an initial round of stimulation because a patient's meibomian glands may have been previously unblocked during the initial stimulation round. In some variations, subsequent rounds of stimulation may be delivered repeatedly over an extended period of time, such as but not limited to at least 30 days, at least 45 days, at least 60 days, or at least 90 days. For example, subsequent rounds of stimulation may be delivered at least once daily over the extended period of time.

The subject may optionally be instructed to blink during intranasal stimulation. Blinking while the intranasal stimulation is delivered may result in greater meibum secretion. In some variations, the subject may be instructed to blink forcefully during intranasal stimulation. The subject may be instructed, for example, to blink forcefully about every 1 second, about every 2 seconds, about every 3 seconds, about every 5 seconds, about every 10 seconds, about every 15 seconds, about every 20 seconds, about every 30 seconds, about every 1 minute, or the like.

The initial round of stimulation may in some methods be performed under the supervision of a medical professional, while subsequent rounds of stimulation may be performed without supervision of a medical professional (e.g., at home). Generally, as described herein, the waveforms used for the initial round of intranasal stimulation may be configured to generate a stronger sensation than the waveforms used for at-home stimulation. In some variations, the initial and subsequent rounds of stimulation may be delivered using different stimulators. These stimulators may be configured with different waveforms, and/or may have different physical configurations. For example, the initial round of stimulation may be delivered using a stimulator configured for hands-free use (e.g., may comprise nasal insertion prongs biased toward each other and/or a strap to hold the nasal insertion prongs in a subject's nose), while subsequent rounds of stimulation may be delivered using a stimulator not configured for hands-free use (e.g., a stimulator having parallel nasal insertion prongs and not comprising a strap). As another example, a stimulator used under supervision of a medical professional (e.g., for an initial round of stimulation) may be fully disposable, while a stimulator used without such supervision (e.g., for subsequent stimulation rounds) may be at least partially reusable.

In general, whereas aqueous tear production may be readily sensed by a subject, the subject may not be able to identify when meibum is being secreted. Accordingly, the methods may comprise obtaining feedback relating to the efficacy of the delivered stimulation. This feedback may provide information confirming that the stimulation is having a desired effect. For example, in some variations, the methods may comprise visual feedback, such as by visualizing the eyelid margin during intranasal stimulation. The eyelid margin may be visualized to assess whether meibum has begun to be secreted out of the meibomian gland openings. For example, the initial round of stimulation may be delivered in a medical professional's office, and the medical professional may visualize the eyelid margin during stimulation to confirm expression of meibum onto the eyelid margin. In some of these methods, for example, the medical professional may visualize the eyelid margin using a slit lamp. As another example, the medical professional may visualize the eyelid margin using an infrared camera (i.e., to determine heating). As yet another example, the medical professional may use a visualization technique capable of assessing the amount or thickness of lipid in the tear film. The medical professional may observe the eyelid margin during stimulation, and stimulus delivery may be continued until meibum expression is seen. After meibum begins to be secreted, the stimulation may be discontinued after a delay period (e.g., the medical professional may discontinue stimulus delivery, or the medical professional may instruct the patient to discontinue stimulus delivery). More specifically, stimulation may be discontinued after the medical professional determines that no new meibum is appearing at the orifice of the meibomian glands. In some variations the stimulus delivery may be continued for at least about 5 minutes, and up to about 10 minutes total.

As another example, the methods may comprise feedback relating to the efficacy of the delivered electrical stimulation by measuring impedance or an electromyogram (EMG) signal. Impedance may reflect the efficacy of the delivered electrical stimulation by indicating that sufficient current is able to flow from the stimulator into tissue. An EMG signal may reflect the efficacy of the delivered electrical stimulation because in some instances, neural stimulation of the anterior ethmoidal nerve may trigger muscle contractions of the orbicularis oculi and/or muscles on the cheek and of the nose as the patient controls an urge to sneeze. As such, EMG signals measured from facial muscles of the nose, cheeks, and/or around the eyes (e.g., the orbicularis oculi) may provide feedback relating to the efficacy of the stimulation for meibum secretion.

These forms of feedback, such as impedance or an EMG signal may be used, for example, to confirm that a stimulus is being effectively delivered for the intended stimulation duration. For example, this feedback may be used to confirm that the stimulus is being effectively delivered at the beginning of a round of stimulation and/or at one or more time points during the round of stimulation. When a round of stimulation has a particular length (e.g., at least 1 minute, at least 3 minutes, at least 5 minutes, at least 10 minutes), these forms of feedback may be used to confirm that the full duration of effective stimulation is delivered. As described herein, intranasal stimulation may cause massaging of the meibomian glands due to contractions of eyelid muscles, and may cause warming of the meibomian glands, which may loosen and reduce the viscosity of meibum and ultimately allow meibum to be secreted onto the eyelid margin; however, in a patient with significantly obstructed meibomian glands, longer stimulation may be needed to achieve a noticeable effect. For example, an initial round of stimulation may have a duration of between about 5 and 10 minutes. In some of these variations, an initial round of stimulation may have a duration of between about 5 and 7 minutes, between about 7 and 10 minutes, or between about 7 and 8 minutes. Subsequent rounds of stimulation after an initial stimulation may be shorter, for example, about 1 to 3 minutes. These subsequent rounds may not need to be as long as an initial round of stimulation because a patient's meibomian glands may have been previously unblocked during the initial stimulation round. As such, it may be desirable to confirm that stimulation is effectively delivered for the full desired duration.

In some instances, feedback, such as an impedance and/or EMG signal, may be measured using the same device that delivers the electrical stimulation. For example, the stimulators described herein may be configured to measure impedance and/or an EMG signal at or near the stimulus delivery electrodes. In other instances, the impedance and/or EMG signal may be measured using a separate device (i.e., not the same device as the device that delivers the electrical stimulation). For example, the impedance and/or EMG signal may be measured by a separate intranasal or extranasal device. In some variations, the extranasal device may comprise a nose strip comprising detection electrodes placed on the outside of the nose.

In some variations, the methods may comprise modifying the stimulation location and/or stimulus parameters based on feedback. For example, in variations using visual feedback, a medical professional may choose to modify the stimulus parameters during stimulation based on the visualization. When the stimulator comprises a remote interface, the medical professional may adjust the stimulus parameters during stimulation him/herself. When the stimulator does not comprise a remote interface and comprises only a user interface on the stimulator body, the medical professional may instruct the subject to adjust the stimulation parameters during stimulation. The stimulus parameters may be adjusted, for example, to achieve more meibum expression and/or more uniform meibum expression between the left and right eyes, and/or to adjust the sensation perceived by the subject. Stimulus parameters that may be adjusted include stimulus waveform parameters and/or location of stimulus delivery (including via modulating the electrodes between which current travels). For instance, if the medical professional observes that the intranasal stimulation is resulting in more expression from meibomian glands of one eye as compared to the other, and/or that the intranasal stimulation is resulting in more heating of tissue near one eye as compared to the other, the medical professional may adjust or instruct the subject to adjust the parameters to achieve more uniform expression (e.g., modify the waveform such that the side of the nasal cavity corresponding to the eye with less meibum expression or lower temperature is stimulated more than the other side of the nasal cavity).

As another example, in variations using an impedance and/or EMG signal, the stimulation location and/or stimulus parameters may be modified based on the impedance and/or EMG signal. In some variations, the duration of a round of stimulation may be increased to account for a detected period of inadequately effective stimulation delivery, such that the full intended duration of effective stimulation is delivered. In other variations, the impedance and/or EMG signal may be used to adjust stimulation parameters such as stimulus waveform parameters and/or location of stimulus delivery (including via modulating the electrodes between which current travels).

Intranasal stimulation may optionally be used in conjunction with other therapies for treatment of meibomian gland disease/dysfunction and/or for treatment of blepharitis. For example, patients receiving intranasal stimulation may also be treated with eyelid hygiene (e.g., warming, massaging, heated compresses, and/or cleaning of eyelids), topical treatments (e.g., artificial lubricants (e.g., lipid-based artificial tears), topical steroids, topical cyclosporine, topical azithromycin, topical antibiotics (e.g., bacitracin)), oral antibiotics (e.g., oral tetracycline, oral doxycycline), nutritional supplements (e.g., fish oil, gamma-linolenic acid), meibomian gland probing by a medical professional, environmental changes (e.g., increased humidity), simultaneous application of heat and pulsatile pressure to the eyelids, or the like. For example, in some variations lid hygiene techniques may be used after delivery of intranasal stimulation to remove any meibum plugs expelled during stimulation. Intranasal stimulation may then be delivered again after lid hygiene techniques to help reestablish a full tear film.

EXAMPLES

Example #1

Acute Meibum Secretion

A study was conducted to evaluate the effect of intranasal stimulation on meibum secretion in subjects with dry eye disease (DED) by visual assessment of various measures of meibomian gland function and assessment of tear meniscus height and tear meniscus area.

Twenty-five DED subjects were enrolled. Subjects were selected to have a baseline Ocular Surface Disease Index score of at least 13, with no more than three responses of "not applicable"; in at least one eye, a baseline Schirmer's test with anesthetic of less than or equal to 10 mm over 5 minutes, and in the same eye, a Schirmer's test that was at least 7 mm higher with cotton swab nasal stimulation; in at least one eye, a lower eyelid margin meibum quality global assessment score of greater than or equal to 1 and not non-expressible, where the score was based on the summed score for each of eight glands in the central third of the lower lid, where each gland was given a score of 0-3, with 0 for clear meibum, 1 for cloudy meibum, 2 for cloudy meibum with debris, and 3 for thick meibum; in at least one eye, a number of lower eyelid margin meibomian glands expressible by digital or cotton swab palpitation greater than or equal to 3; and use of an artificial tear product or lid hygiene protocol (warm compress, lid massage, and/or lid scrub) for the treatment of dry eye disease or meibomian gland disease/dysfunction within 1 year.

Subjects received either extranasal (control) stimulation or intranasal stimulation for a duration of eight minutes. Stimulation was delivered using a handheld stimulator similar to the stimulator 400 shown in FIGS. 4A-4E. More particularly, each subject was provided with a system comprising a reusable stimulator body configured to produce an electrical stimulation waveform; a disposable stimulator probe configured to be inserted into the subject's nasal cavity and to stimulate the target intranasal tissue, a reusable cap configured to protect the stimulator probe; and a charger configured to recharge a battery within the stimulator body. When activated, the stimulator body provided an electrical stimulus to the stimulator probe. Different electrical stimuli such as the stimuli described herein were available on the stimulator, and the stimulus being delivered was indicated by the number of illuminated light emitting diodes on the stimulator body. The stimulator body was configured such that the electrical stimulus could only be delivered when a stimulator probe was attached to the stimulator body. The stimulator body was configured to record the usage of the stimulator, including the stimulus used and duration, in an internal memory. The stimulator probe comprised a hydrogel configured to contact the inside of the nose to deliver the electrical stimulus. The disposable stimulator probes were configured to be removably attached to the stimulator body and to be replaced periodically (e.g., at least once daily). The stimulator body was rechargeable by removing a stimulator probe from the stimulator body and placing the stimulator body onto the base station. Charging status of the device was indicated by illumination of a light emitting diode.

Figure 13A:
FIG. 13A shows a handheld stimulator inserted into a subject's nose.
Figure 13B:
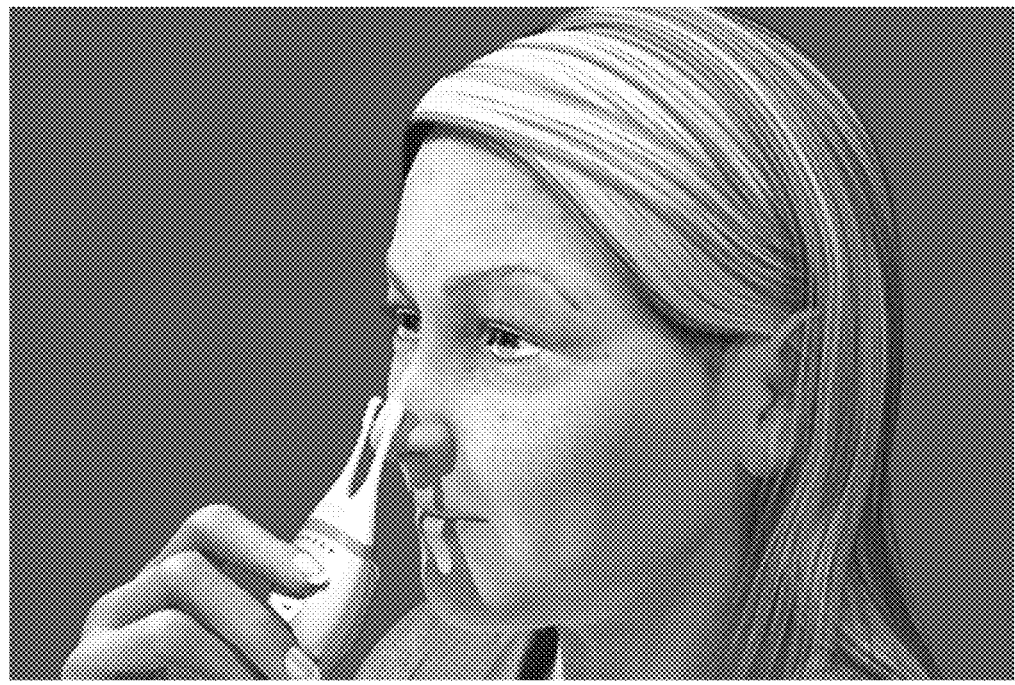
FIG. 13B shows a handheld stimulator held in position for extranasal (control) stimulation.

For subjects receiving intranasal stimulation, each subject was instructed to hold the stimulator body and insert the stimulator probe into his or her nostrils simultaneously, as shown in FIG. 13A. For subjects receiving extranasal (control) stimulation, each subject was instructed to place the tips of the stimulator probe on the lower part of the nose (not within the nostrils), with one tip on each side of the nose, as shown in FIG. 13B. Each subject used plus (+) and minus (−) buttons on the stimulator body to turn on and control an electrical stimulus between the available stimuli. Subjects were instructed to adjust the stimulus and location of stimulus delivery until paresthesia was perceived. Each subject applied stimulation for eight minutes. During the first two minutes of stimulation, the subject was positioned at a slit lamp for imaging of the subject's eyelids for the number of meibomian glands secreting. During the next one minute, the subject was positioned at an optical coherence tomograph to measure tear meniscus height and tear meniscus area. During the remaining five minutes, the subject was repositioned at the slit lamp for imaging of the subject's eyelids.

Various assessments were made before and during administration of intranasal stimulation. More particularly, lid margin assessments were made of the lower eyelid, lower central meibomian gland, as well as tear film temperature through thermal video capture. Lipid layer thickness was also measured prior to and immediately after intranasal stimulation. Eyelid videography was used to assess secretion viscosity, secretion color, the number of secreting glands, eyelid margin redness, hyperkeratinization, meibum on posterior eyelid edge, the tear film, perigland redness, lash loss, mucocutaneous junction, and meibomian gland alignment, geometry, and height. The central 15 meibomian glands of each eye were assessed.

Figure 14A:
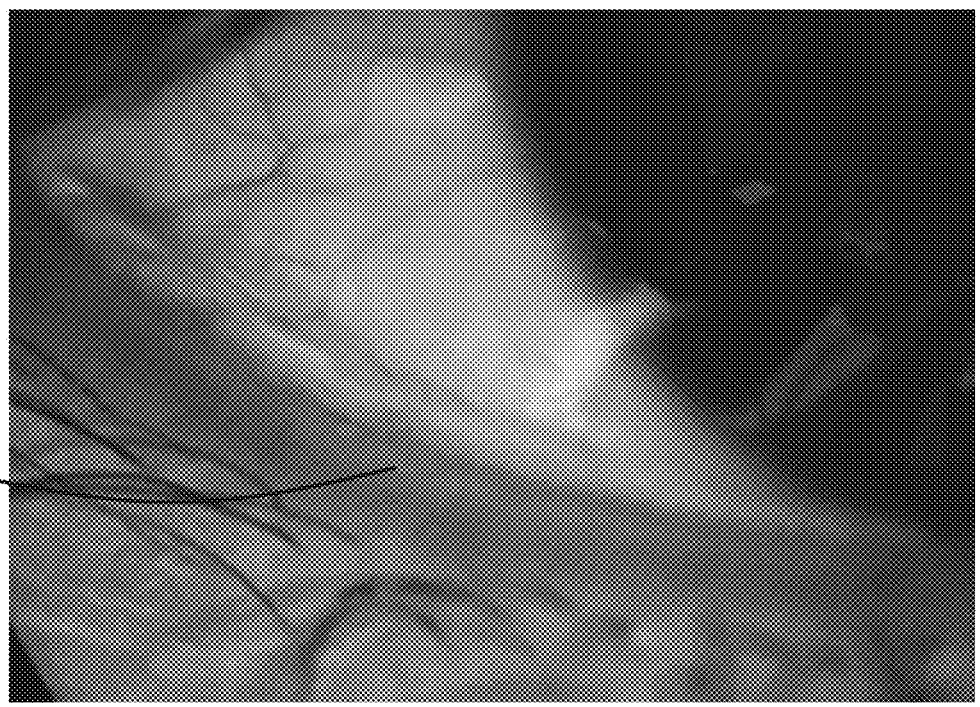
FIGS. 14A-14B show images of the lower eyelid of a subject before and after 1 minute of intranasal stimulation, respectively.
Figure 14B:
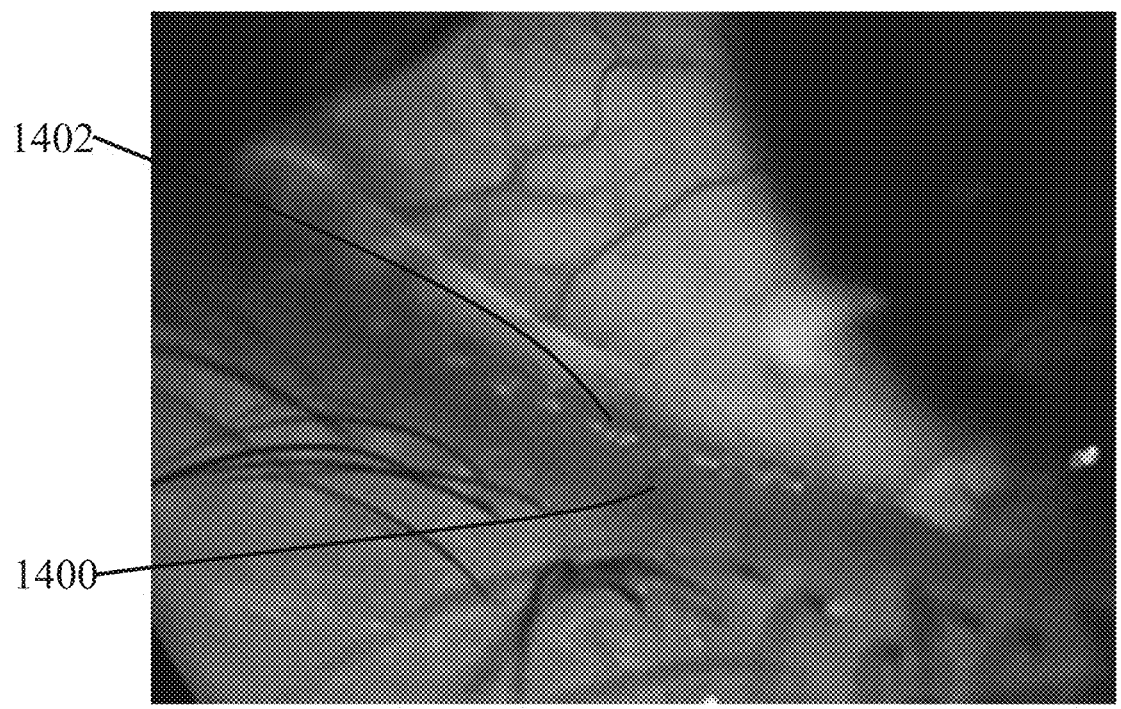
Figure 14C:
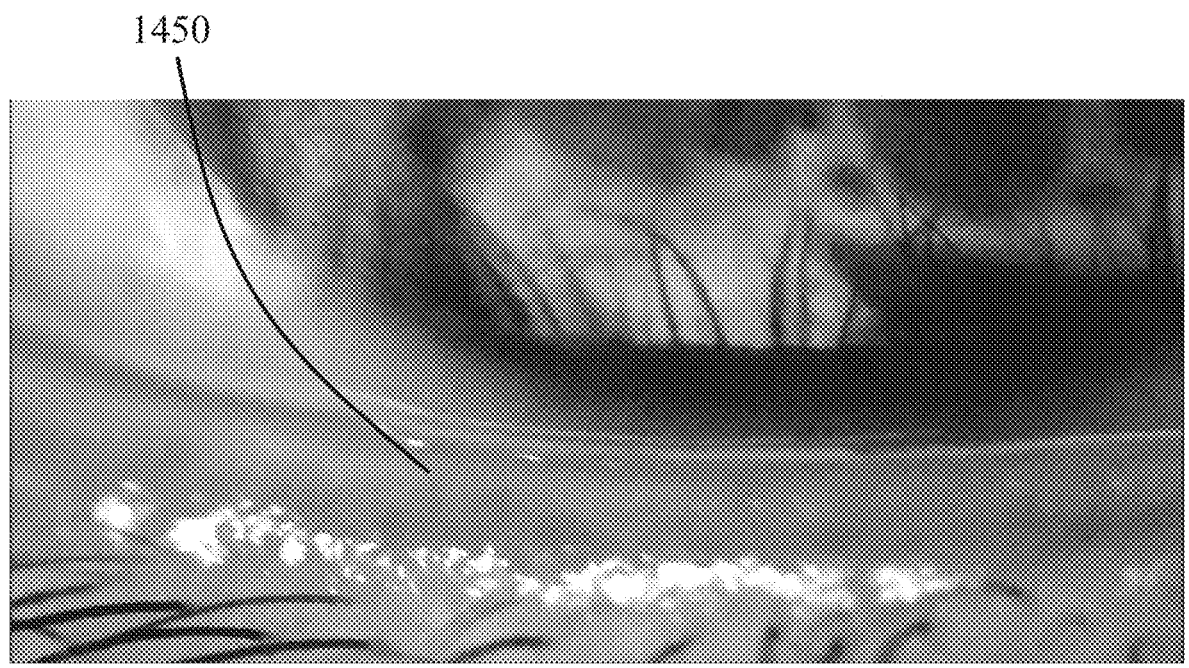
FIGS. 14C-14D show images of the lower eyelid of another subject before and after intranasal stimulation, respectively.
Figure 14D:
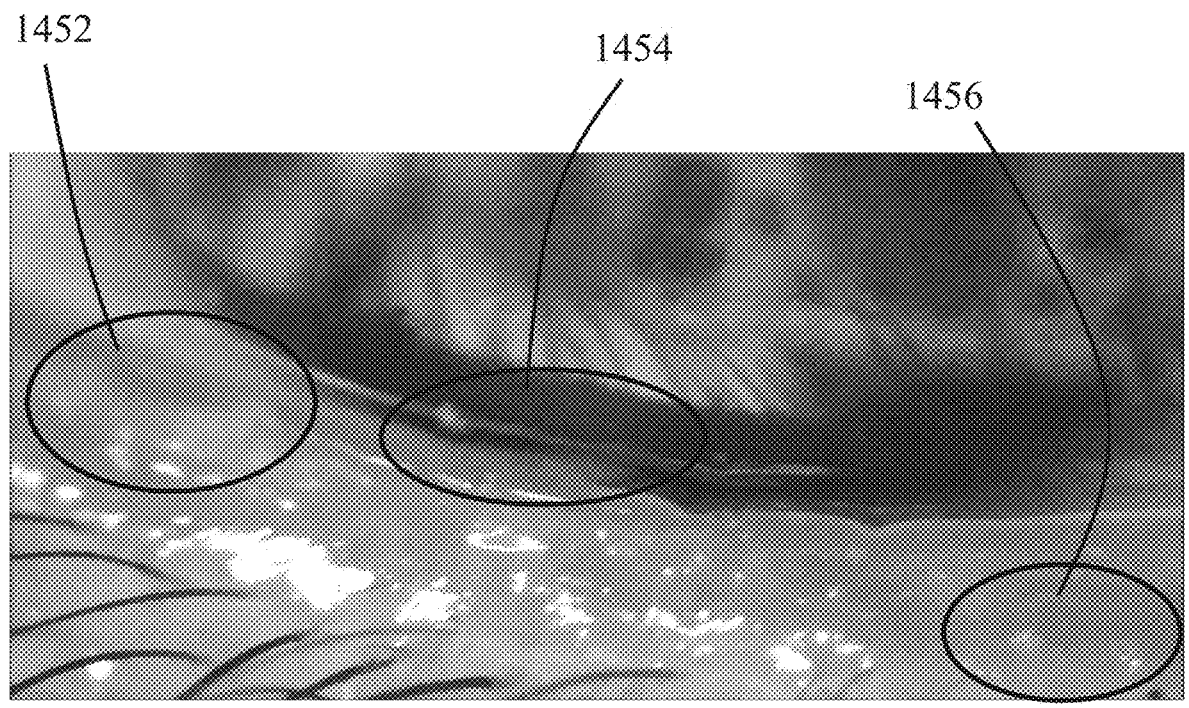

It was expected that the number of secreting glands is greater during administration of intranasal stimulation as compared to before intranasal stimulation. Initial results show that the number of secreting glands increases during intranasal stimulation: FIGS. 14A-14B show images of the lower eyelid 1400 of a subject before and after 1 minute of intranasal stimulation, respectively. As can be seen there, secreted meibum 1402 is visible during intranasal stimulation. Similarly, FIGS. 14C-14D show images of the lower eyelid 1450 of a subject before and after intranasal stimulation, respectively. As can be seen there, the portion 1452 of the lower eyelid 1450 shows secreted, thick meibum (grade 2 or 3 on the scale described above); the portion 1454 of the lower eyelid 1450 shows floaters (ejected difficult-to-express meibum); and the portion 1456 of the lower eyelid 1450 shows plugged meibomian glands beginning to express meibum.

Figure 18A:
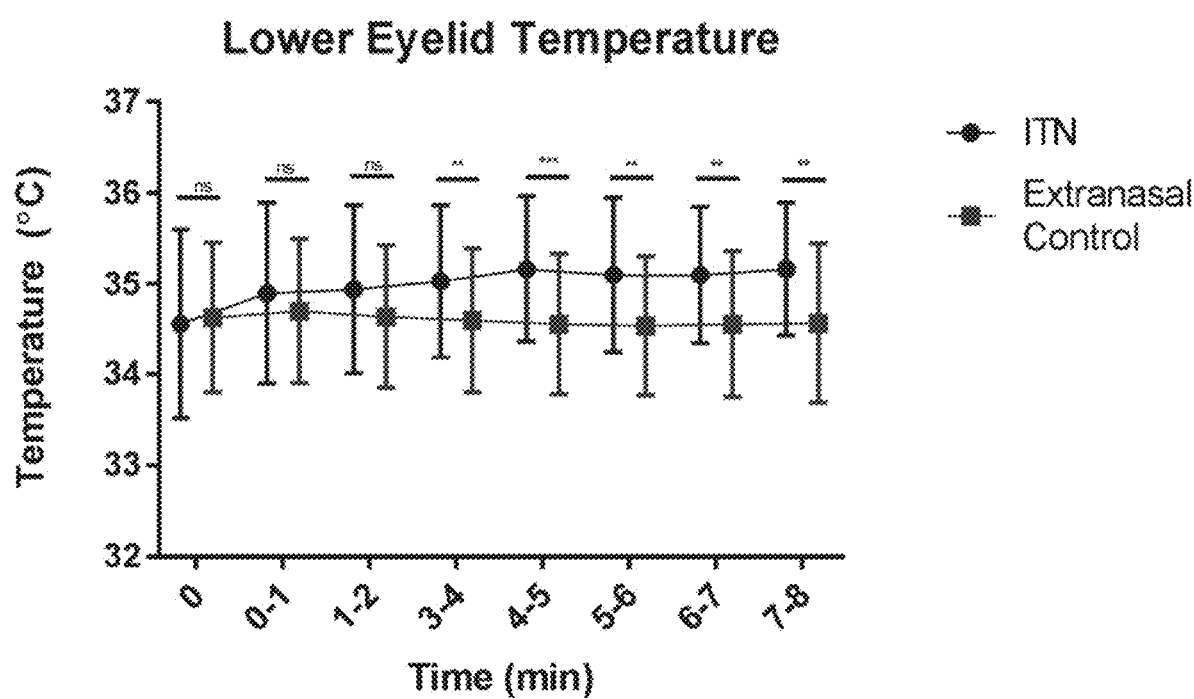
FIGS. 18A-18C are graphs of mean temperatures for the lower lid, lower central meibomian glands, and tear film during intranasal stimulation and extranasal (control) stimulation.
Figure 18B:
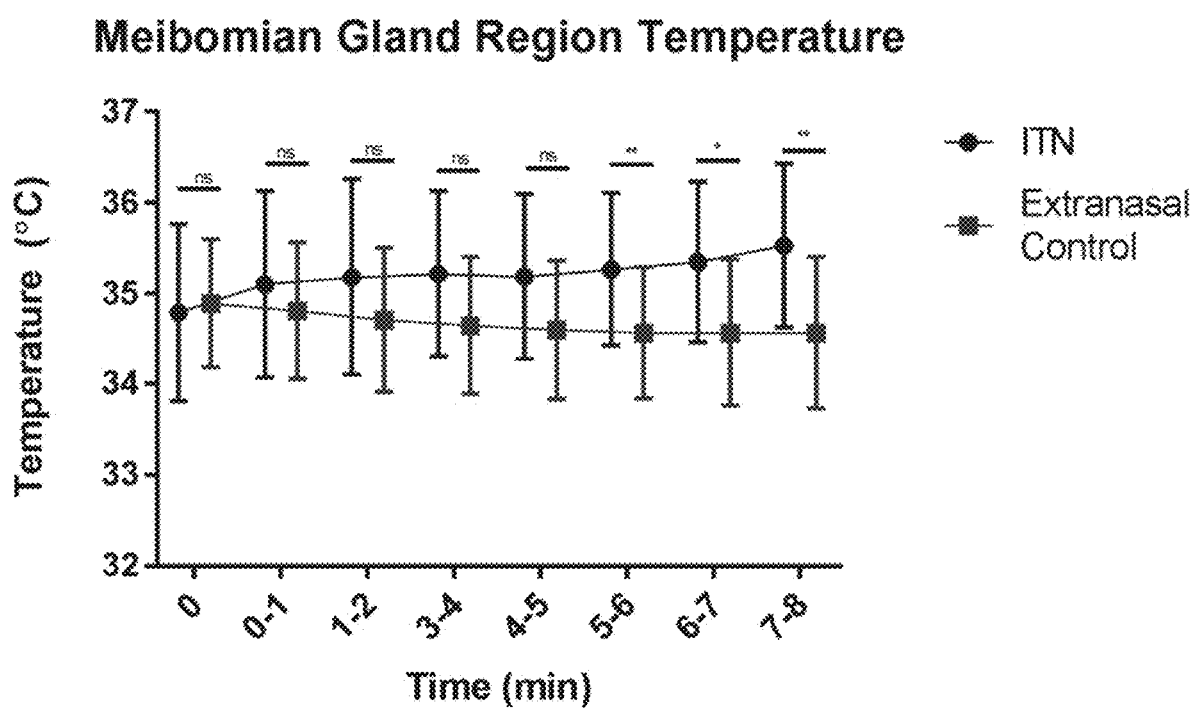
Figure 18C:
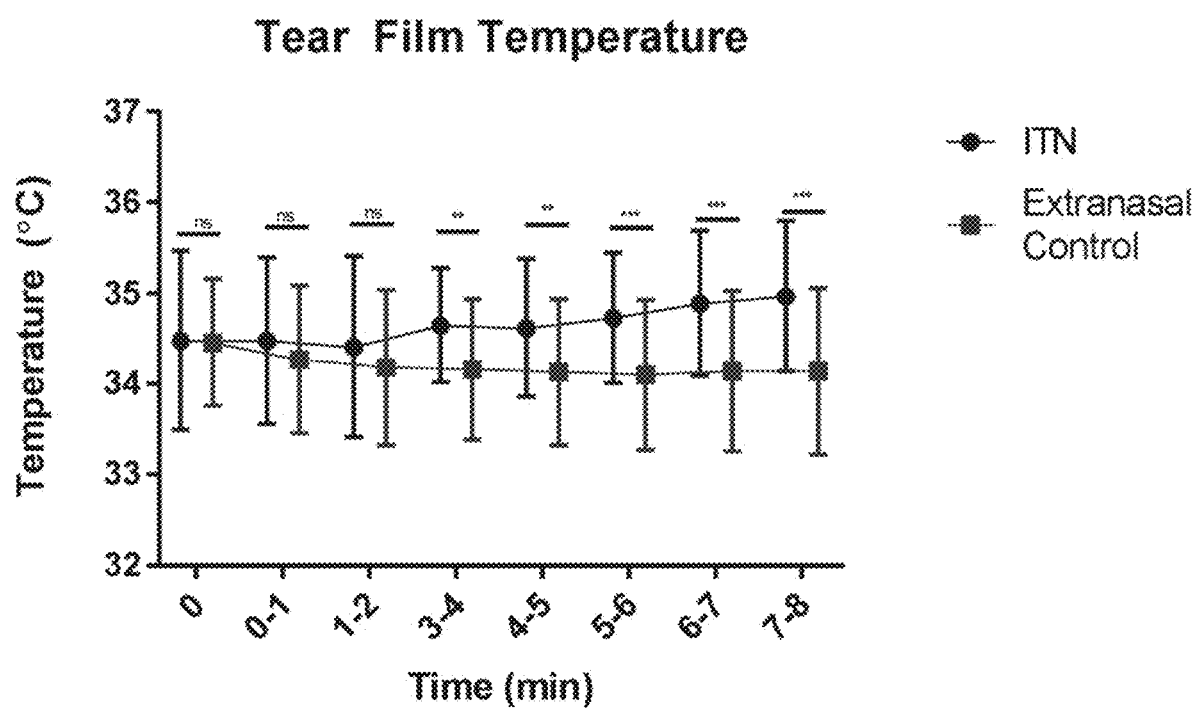

The lower lid temperature, lower central meibomian gland temperature, and tear film temperature were all found to have a statistically significant increase with intranasal stimulation as compared to the extranasal control (during the last minute of stimulation as compared to immediately prior to stimulation). For the lower lid, the change in temperature was 0.61° C.±0.33° C. with intranasal stimulation and −0.07° C.±0.63° C. with the control, with a paired difference of change of 0.69° C.±1.17° C. ($p=0.016$). For the lower central meibomian glands, the change in temperature was 0.57° C.±0.82° C. with intranasal stimulation and −0.32° C.±0.56° C. with the control, with a paired difference of change of 0.88° C.±0.91° C. ($p<0.001$). For the tear film, the change in temperature was 0.49° C.±0.93° C. with intranasal stimulation and −0.32° C.±0.67° C. with the control, with a paired difference of change of 0.80° C.±1.09° C. ($p=0.004$). Mean temperatures for the lower lid, lower central meibomian glands, and tear film during intranasal stimulation and extranasal (control) stimulation are shown in FIGS. 18A-18C, respectively. The difference between the mean temperature with intranasal stimulation ("ITN") and extranasal (control) stimulation is indicated as "ns" (not significant), "*" ($p<0.05$), "" ($p<0.01$), or "*" ($p<0.001$). Significance was reached at the 3-4 minute time point and onward for tear film temperature and lower lid temperature during stimulation, and the greatest separation between treatment groups occurred at the 8-minute mark for all three of the lower lid, lower central meibomian gland, and tear film temperatures. Additionally, when comparing the mean change in temperature from immediately prior to stimulation to during the last minute of stimulation, all three of the lower lid, lower central meibomian gland, and tear film temperatures increased for the group receiving intranasal stimulation, whereas the temperatures decreased for the group receiving extranasal (control) stimulation.

It was further expected that meibum content of the tear film would increase during administration of intranasal stimulation as compared to before intranasal stimulation. Measurement of the lipid layer thickness was found to increase with intranasal stimulation. The change in thickness (after stimulation as compared to immediately prior to stimulation) was found to be 0.91±0.73 with intranasal stimulation and 0.35±0.65 in the control, with a paired difference of change of 0.57±1.16 ($p=0.029$).

Thus, the increase in temperature of the lower eyelid, lower central meibomian gland, and tear film, as well as the increase in lipid layer thickness, demonstrated that intranasal stimulation results in both lacrimal and meibomian gland secretion. It is also expected that the non-invasive tear film breakup time will improve (i.e., increase) during administration of intranasal stimulation as compared to before intranasal stimulation, and optical coherence tomography will demonstrate increased tear meniscus height and area during intranasal stimulation.

Example #2

Meibomian Gland Morphology

A study was conducted explore the effect of intranasal stimulation on meibomian gland morphology. Anterior segment optical coherence tomography (AS-OCT) meibography was performed on the lower eyelids of each of twelve dry eye subjects before and after three minutes of intranasal stimulation. Intranasal stimulation was delivered using a handheld stimulator similar to the stimulator 400 shown in FIGS. 4A-4E and described in more detail with respect to Example #1. The area and perimeter of selected meibomian glands were quantified, and the effect of intranasal stimulation on meibomian glands was determined by morphological changes after stimulation. Within the selected images, three to four glands were analyzed. Central meibomian glands clearly shown in both sets of AS-OCT images were selected for analysis, according to the accuracy and quality of the image, and the same meibomian glands were selected before and after stimulation. The area and perimeter of selected meibomian glands were analyzed by two masked observers using Image™ software.

The intranasal stimulation was found to have a significant effect on meibomian gland morphology. After intranasal stimulation, meibomian glands were measurably reduced in area and perimeter, suggesting that intranasal stimulation causes release of meibum from within the glands. Mean pre- and post-stimulation meibomian gland areas were 2,184.76±135.51 $\mu m^2$ and 1,933.2±114.82 $\mu m^2$, respectively. The mean change in area, 251.56±20.69 $\mu m^2$, representing an 11.6% reduction following intranasal stimulation, was statistically significant ($p<0.001$). Mean pre- and post-stimulation meibomian gland perimeters were 235.9±10.95 $\mu m$ and 222.2±10.14 respectively. The mean change in perimeter, 13.7±0.81 $\mu m$, representing a 5.81% reduction following intranasal stimulation, was statistically significant ($p<0.012$). The images after intranasal stimulation showed an increase in brightness at the conjunctival surface, and hyporeflective areas at orifices of the meibomian glands suggesting release of meibum.

Example #3

Tear Composition

A study was conducted on subjects with dry eye disease to evaluate acute tear production and the relative concentration of total lipid in tears collected pre- and post- a single treatment period with intranasal stimulation. This study thus indirectly tested for increased meibum secretion after intranasal stimulation, since an increase in acute tear production with a sustained or increased concentration of lipids indicates increased absolute meibum secretion.

Subjects were selected to have a baseline Ocular Surface Disease Index score of at least 13, with no more than three responses of "not applicable"; and in at least one eye, a baseline Schirmer's test with anesthetic of less than or equal to 10 mm over 5 minutes, and in the same eye, a Schirmer's test that was at least 7 mm higher with cotton swab nasal stimulation. Fifty-five subjects were enrolled in the study, and forty-one subjects (26 females and 15 males; mean age of 61.6±15.9 years (26 to 86); mean OSDI score of 43.0±19.8 (16.7 to 83)) provided sufficient baseline (pre-) and post-stimulation tear samples for analysis.

Prior to intranasal stimulation, each subject had, for each eye, tear volume assessed and tear samples collected. Tear volume was assessed using tear meniscus height. Tear meniscus height was captured using optical coherence tomography. Tear samples of up to 10 μL were collected (up to 5 μL from each of the left and right eyes, pooled). Tear samples were collected using a microcapillary tube from the tear lake near the temporal canthus without touching the globe. Total lipid concentration in the tear samples was determined using a modified spectrophotometric sulfo-phospho-vanillin reaction.

Subjects received approximately three minutes of intranasal stimulation delivered using a handheld stimulator similar to the stimulator 400 shown in FIGS. 4A-4E and described in more detail with respect to Example #1. Approximately five minutes after the approximately three minutes of stimulation, tear meniscus height was again recorded for each eye using optical coherence tomography, and up to 10 μL of tear samples were again collected (up to 5 μL from each of the left and right eyes, pooled).

Tear samples were stored in a in a −80° C. freezer. Tear lipids were extracted using chloroform:methanol (2:1) extraction before performing a sulpho-phospho-vanillin assay (SPVA). An aliquot of tear sample was transferred to a glass vial and water was added to make up the total volume to 10 μL. Chloroform:methanol (2:1) was added 20× the volume of the tear aliquot. Samples were let to stand at room temperature for 10 min. 15 μL of water was then added, vortexed, and let to stand for 5 min. The samples were then centrifuged to separate the organic and aqueous layers. The organic layer was then carefully transferred to a 96-well plate to perform the SVPA.

To perform the SVPA, a 5 mg/mL stock of each lipid standard was prepared in chloroform. A calibration curve consisting of a mixture of lipids to mimic lipids found in the tear film was prepared as shown in Table 1.

TABLE 1

List of lipids and ratio by weight for the calibration curve standard.

| Lipid | Ratio by Weight |
|---|---|
| Behenyl oleate | 0.41 |
| Behenyl stearate | 0.08 |
| Cholesteryl stearate | 0.40 |
| Cholesteryl oleate | 0.10 |
| Free cholesterol | 0.01 |

The calibration curve concentrations ranged from 0 to 4 mg/mL. Defined aliquots of calibration curve standards, in triplicate, were transferred to a glass-coated 96-well plate and then evaporated to dryness. The lipids extracted from tears were added to the glass-coated 96-well plate. 100 μL sulphuric acid (95%) was added to the wells and heated at 95° C. for 20 min. Absorbance at 540 nm (pre-vanillin absorbance) was measured in triplicate. 50 μL of vanillin solution prepared in 60% phosphoric acid was added to the wells. The samples were incubated in the dark for 10 minutes, and the absorbance at 540 nm was measured again in triplicate. The final results were determined by the difference between the post-vanillin and pre-vanillin average absorbance readings.

Mean pre- and post-stimulation tear meniscus heights were 238.4±131.9 μm and 634.9±471.2 μm, respectively. The mean tear meniscus height increased following stimulation, representing an increase in tear production. More specifically, the mean difference in tear meniscus height was 396.5±459.0 μm, representing a 166% increase in tear production following stimulation, and was statistically significant ($p<0.001$). Mean pre- and post-stimulation lipid concentrations were 0.391±0.30 m/μL and 0.364±0.25 m/μL, respectively. An equivalence margin of ±0.078 μg/μL (20% of the pre-stimulation mean) was used to evaluate the equivalence of the pre- and post-stimulation total lipid concentration. The 95% confidence interval of the mean difference in total lipid concentration (−0.016±0.18 μg/μL) fell within the equivalence margin [95% CI: −0.074, 0.042].

The results indicated that the intranasal stimulation resulted in a significant increase in tear volume with an equivalent concentration of total lipid as compared to subjects' basal tears, suggesting that the stimulation resulted in increased lipid content in addition to aqueous tear production. That is, the relative concentration of total lipid in tears collected after intranasal stimulation was the same as in tears collected before intranasal stimulation, thus indicating an increase in meibum secretion after intranasal stimulation.

Figure 15:
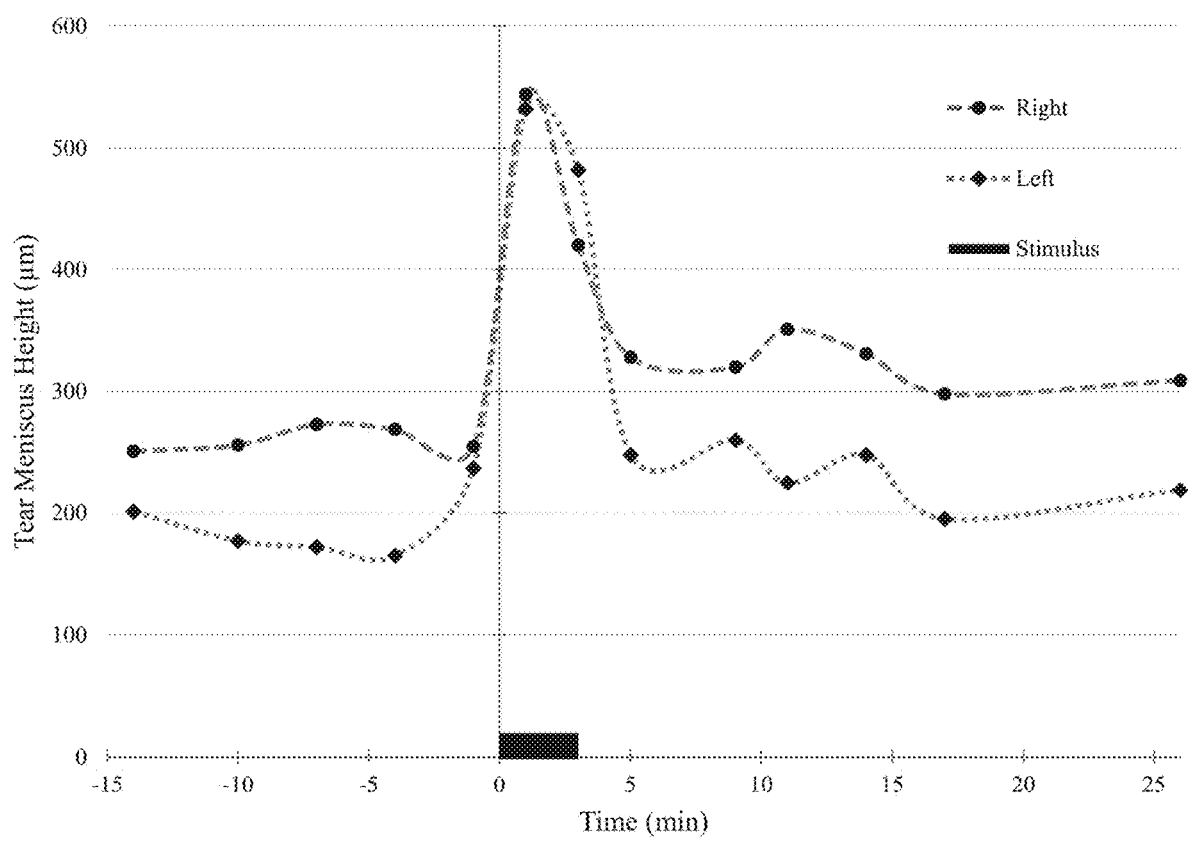
FIG. 15 is a graph of tear meniscus height over time before, during, and after intranasal stimulation.

The results also indicated that in some instances tear meniscus height was elevated by a factor of about two during intranasal stimulation, and elevated by about 25% in the period after intranasal stimulation (15 minutes after stimulation). FIG. 15 is a graph of tear meniscus height over time before, during, and after intranasal stimulation for one subject. As shown there, the tear meniscus height on the right eye increased by about 25% after stimulation, and the tear meniscus height on the left eye increased by about 24% after stimulation.

Example #4

Treatment Protocol

In one exemplary treatment protocol, a patient having meibomian gland disease/dysfunction may initially receive in-office treatment. The patient may be placed in front of a slit lamp or other device for visualizing the lower eyelid and/or tear film. A stimulator as described herein (e.g., stimulator 400 shown in FIGS. 4A-4E) may be placed in the patient's nose. The stimulator may be configured for handheld or hands-free use. Electrical stimulation may be delivered to the nasal mucosa using the stimulator for at least 3 minutes, and up to a maximum of 10 minutes.

While intranasal stimulation is delivered, the medical professional may observe the patient's eyes and note when tear meniscus height increases. In some instances, this may occur after approximately 10 to 30 seconds of stimulation. The medical professional may also observe the patient's meibomian glands during stimulation by observing the lower eyelid margin and/or upper eyelid margin, and/or may observe the tear film thickness. The medical professional may note meibum secretion and/or increased meibum secretion from the meibomian glands onto the eyelid margin. This effect will generally occur after an increase in tear meniscus height (i.e., after secretion of aqueous tears). In some instances, this may occur after approximately 1 to 5 minutes. The medical professional may also note release of meibum plugs from the openings of the glands. After approximately 5 to 8 minutes of stimulation after meibum secretion and/or increased meibum secretion is observed, the stimulation may be stopped.

Following the initial in-office treatment, the patient may continue to self-administer at-home stimulation. The patient may self-administer intranasal stimulation using the same stimulator used for the in-office treatment, or may use a different stimulator. The patient may be instructed to apply intranasal stimulation at least twice daily, and more as needed. During these subsequent rounds of stimulation, the patient may stimulate for up to 3 minutes. The stimulus parameters used for continuing at-home treatment may be different from the parameters used for in-office treatment. For example, the stimulus parameters used for continuing at-home treatment may have lower maximum amplitude and shorter on/off periods.

After a period of in-home stimulator use (e.g., about 1 month, 2 months, 3 months, etc.), the patient may optionally receive a second in-office treatment as described above. Additionally or alternatively, after a period of in-home stimulator use, a medical professional may observe the patient's lower and/or upper eyelid margin during delivery of the same stimulation waveforms as used for in-home stimulation. The medical professional may observe the duration of stimulation at which meibum begins to be secreted onto the eyelid margins. The patient may be instructed to deliver intranasal stimulation for at least this duration during each round of stimulation in subsequent in-home use.

Example #5

Chronic Intranasal Stimulation

A study will be conducted to evaluate the efficacy of intranasal stimulation over a period of 30 days for the treatment of meibomian gland disease/dysfunction. Subjects will be randomized into treatment groups receiving (1) intranasal stimulation or (2) moist heat compress treatment (control). Subjects will apply either intranasal stimulation or moist heat compress daily for a period of approximately 30 days.

For subjects in the intranasal stimulation treatment group, intranasal stimulation will be delivered using a handheld stimulator similar to the stimulator 400 shown in FIGS. 4A-4E and described in more detail with respect to Example #1. At an initial in-office treatment, each subject will have intranasal stimulation delivered for approximately eight minutes. For subsequent at-home treatment, subjects will be instructed to deliver intranasal stimulation at least twice daily. During these at-home rounds of stimulation, the patient may stimulate for up to 3 minutes, not to exceed 30 total minutes per 24-hour period.

Study measures will include questionnaires related to frequency and severity of dry eye symptoms and symptoms associated with meibomian gland disease/dysfunction; lipid layer thickness; temperatures of the lower lid margin, tear film, and lower central meibomian glands; lower lid meibomian gland assessment, including number of secreting glands and meibum quality; lower lid meibography to assess numbers of full glands in lower lid margin, partial glands in lower lid margin, and missing glands in lower lid margin; and lid appearance. Meibum quality will be assessed based on a score of 0-3, with 0 for clear meibum, 1 for cloudy meibum, 2 for cloudy meibum with debris, and 3 for thick meibum. Study measures will be assessed at various time points throughout the 30 day period.

It is expected that intranasal stimulation over the 30-day period will provide efficacious treatment of meibomian gland disease/dysfunction, as compared to the control group, as measured by signs and/or symptoms of meibomian gland disease/dysfunction. It is expected that at the completion of the 30-day period, patients in the intranasal stimulation treatment group will have greater lipid layer thickness, as compared to the control group. It is further expected that at the completion n of the 30-day period, patients in the intranasal stimulation treatment group will have a higher number of secreting lower lid meibomian glands, as compared to the control group. It is further expected that at the completion of the 30-day period, patients in the intranasal stimulation treatment group will have improved meibum quality, as compared to the control group. It is further expected that at the completion of the 30-day period, patients in the intranasal stimulation treatment group will have improved lower eyelid appearance, as compared to the control group. It is further expected that at the completion of the 30-day period, patients in the intranasal stimulation treatment group will have improved symptoms, as compared to the control group.

The invention claimed is:

1. A method for treating a subject, comprising:
applying or instructing the subject to apply a heat source to an eyelid of the subject prior to delivering or instructing the subject to deliver an intranasal electrical stimulation to the subject;
delivering or instructing the subject to deliver the intranasal electrical stimulation to the subject in conjunction with and after applying or instructing the subject to apply the heat source to the eyelid of the subject;
measuring or instructing the subject to measure, during the delivery of the intranasal electrical stimulation, an impedance or an electromyogram signal from a facial muscle of the subject;
providing, based on the impedance or the electromyogram signal, feedback relating to an efficacy of at least the delivered intranasal electrical stimulation;
visualizing an eyelid margin of the subject during the intranasal electrical stimulation of the subject; and
stopping or instructing the subject to stop the delivery of the intranasal electrical stimulation after observing secretion of meibum onto the eyelid margin,
wherein the subject has meibomian gland disease.

2. The method of claim 1, wherein the eyelid margin is visualized using a slit lamp.

3. The method of claim 1, further comprising adjusting at least one parameter of the intranasal electrical stimulation during the visualization of the eyelid margin.

4. The method of claim 1, wherein the intranasal electrical stimulation is delivered by a stimulator comprising a nasal insertion prong, wherein a portion of the nasal insertion prong is in contact with nasal mucosa of the subject.

5. The method of claim 4, wherein the stimulator comprises a user interface configured to adjust at least one parameter of the intranasal electrical stimulation.

6. The method of claim 4, wherein the stimulator comprises a remote interface configured to adjust at least one parameter of the intranasal electrical stimulation.

7. The method of claim 6, further comprising adjusting the at least one parameter of the intranasal electrical stimulation using the remote interface while visualizing the eyelid margin.

8. A method for treating a subject, comprising:
applying or instructing the subject to apply a heat source to an eyelid of the subject, in conjunction with and before delivering or instructing the subject to deliver intranasal electrical stimulation;
measuring, during the intranasal electrical stimulation, an impedance or an electromyogram signal from a facial muscle of the subject to provide feedback relating to an efficacy of at least the intranasal electrical stimulation;
visualizing an eyelid margin of the subject during the intranasal electrical stimulation of the subject; and
adjusting at least one parameter of the intranasal electrical stimulation based on the visualization and the feedback,
wherein the subject has meibomian gland disease.

9. The method of claim 8, wherein a first number of meibomian glands of the subject secreting meibum during the intranasal electrical stimulation is greater than a second number of meibomian glands of the subject secreting meibum before the intranasal electrical stimulation.

10. The method of claim 8, wherein the adjusting of the at least one parameter of the intranasal electrical stimulation comprises changing a first stimulation waveform to a second stimulation waveform, and wherein a first difference between a first number of meibomian glands of a first eye of the subject secreting meibum and a second number of meibomian glands of a second eye of the subject secreting meibum during intranasal electrical stimulation with the first stimulation waveform is larger than a second difference between a third number of meibomian glands of the first eye of the subject secreting meibum and a fourth number of meibomian glands of the second eye of the subject secreting meibum during intranasal electrical stimulation with the second stimulation waveform.

11. The method of claim 8, wherein the intranasal electrical stimulation is delivered by a stimulator comprising a nasal insertion prong, wherein a portion of the nasal insertion prong is in contact with nasal mucosa of the subject.

12. The method of claim 11, wherein the stimulator comprises a remote interface configured to adjust the at least one parameter of the intranasal electrical stimulation.

13. The method of claim 12, further comprising adjusting the at least one parameter of the intranasal electrical stimulation using the remote interface while visualizing the eyelid margin.

14. A method of treating dry eye, comprising:
applying a heat source to an eyelid of the subject prior to intranasally delivering an electrical stimulation to a nasal cavity of the subject;
intranasally delivering the electrical stimulation to the nasal cavity of the subject in conjunction with and after applying the heat source to the eyelid of the subject; and
measuring, during the intranasal delivery of the electrical stimulation, an impedance or an electromyogram signal from a facial muscle of the subject,
wherein the applied heat source and intranasally delivered electrical stimulation is effective to increase meibum secretion, and wherein the measured impedance or the measured electromyogram signal indicate an efficacy of at least the intranasally delivered electrical stimulation for increasing the meibum secretion.

15. The method of claim 14, wherein the duration of the intranasally delivered electrical stimulation is between about three minutes and about five minutes.

16. The method of claim 15, wherein the duration of the intranasally delivered electrical stimulation is verified by the measured impedance or the measured electromyogram signal.

17. The method of claim 14, wherein the heat source comprises a nasal stimulator configured to deliver the electrical stimulation to the nasal cavity of the subject, the electrical stimulation configured to cause increased muscle activity of an orbicularis muscle of the subject, thereby warming meibum of the subject and increasing the meibum secretion of the subject.

18. The method of claim 14, wherein the eyelid of the subject comprises:
a first temperature before the electrical stimulation is intranasally delivered to the subject; and
a second temperature when the electrical stimulation is intranasally delivered to the subject after a period of time,
wherein the second temperature is higher than the first temperature.

19. The method of claim 18, wherein the electrical stimulation is intranasally delivered to the nasal cavity of the subject when the second temperature is higher than the first temperature.

20. The method of claim 14, wherein the electrical stimulation is intranasally delivered to the subject at a first location in the nasal cavity of the subject, thereby indirectly activating an eyelid muscle at a second location to increase meibum secretion, the second location located away from the first location.

21. A method of treating dry eye, comprising:
repeatedly applying a heat source to an eyelid of a subject in conjunction with and prior to delivering intranasal electrical stimulation to the subject over a period of time;
measuring an impedance or an electromyogram signal from a facial muscle of the subject,
wherein the subject has meibomian gland disease,
wherein the applied heat source and the delivered intranasal electrical stimulation is effective to improve secreted meibum quality, and
wherein the measured impedance or the measured electromyogram signal indicate the improvement in the secreted meibum quality.

22. The method of claim 21, wherein the period of time is at least 30 days.

23. The method of claim 22, wherein the intranasal electrical stimulation is delivered at least once daily over the at least 30 days.

24. The method of claim 22, wherein the improvement in secreted meibum quality comprises an increased number of lower lid meibomian glands secreting clear meibum at 30 days as compared to at 0 days.

* * * * *